(12) United States Patent
Uhlmann et al.

(10) Patent No.: US 7,485,421 B2
(45) Date of Patent: Feb. 3, 2009

(54) POLYAMIDE-OLIGONUCLEOTIDE DERIVATIVES, THEIR PREPARATION AND USE

(75) Inventors: Eugen Uhlmann, Glashuetten (DE); Gerhard Breipohl, Frankfurt (DE)

(73) Assignee: Hoechst GmbH, Frankfurt Am Main (DE)

( * ) Notice: Subject to any disclaimer, the term of this patent is extended or adjusted under 35 U.S.C. 154(b) by 231 days.

(21) Appl. No.: 10/939,214

(22) Filed: Sep. 10, 2004

(65) Prior Publication Data

US 2005/0026817 A1 Feb. 3, 2005

Related U.S. Application Data

(60) Division of application No. 09/793,146, filed on Feb. 27, 2001, now Pat. No. 6,919,441, which is a continuation of application No. 08/982,008, filed on Dec. 1, 1997, now abandoned, which is a continuation-in-part of application No. 08/402,838, filed on Mar. 13, 1995, now abandoned.

(30) Foreign Application Priority Data

Mar. 14, 1994 (DE) .................................. P4408528

(51) Int. Cl.
*C12Q 1/68* (2006.01)
*C07H 21/04* (2006.01)
(52) U.S. Cl. ...................... 435/6; 536/24.31; 536/24.32
(58) Field of Classification Search ...................... 435/6; 536/22.1, 24.31, 24.32
See application file for complete search history.

(56) References Cited

U.S. PATENT DOCUMENTS

| 5,516,937 | A | | 5/1996 | Breipohl et al. |
| 5,700,922 | A | * | 12/1997 | Cook .......................... 536/23.1 |
| 6,075,143 | A | | 6/2000 | Breipohl et al. |
| 6,919,441 | B2 | * | 7/2005 | Uhlmann et al. ............ 536/23.5 |

FOREIGN PATENT DOCUMENTS

| EP | 0602524 | 6/1994 |
| EP | 0552766 | 5/2002 |
| EP | 0552767 | 5/2002 |
| GB | 2284208 | 5/1995 |
| WO | WO89/03849 | 5/1989 |
| WO | WO92/02531 | 2/1992 |
| WO | WO92/20702 | 11/1992 |
| WO | WO93/10820 | 6/1993 |
| WO | WO93/24511 | 12/1993 |
| WO | WO97/27206 | 7/1997 |

OTHER PUBLICATIONS

Tong et al. The synthesis of oligonucleotide-polyamide conjugate molecules suitable as PCR primers. J Org. Chem., vol. 58, pp. 2223-2231, 1993.*

Almarsson et al., Molecular Mechanics Calculations of the Structures of Polyamide Nucleic Acid DNA Duplexes and Triple Helical Hybrids, Proc. Nat'l. Acad. Sci., vol. 90, pp. 7518-7522, 1993.

Beck et al., Application o Dioxetane Chemiluminescent Probes to Molecular Biology, Anal. Chem. vol. 62, pp. 2258-2270, 1990.

Berstrom et al., Organoiron Mediated Alkylation of Phosphite Esters: Synthesis of (Dicarbonyl)(n5-Cyclopntadienyl) Iron-Derived Nucleoside Phosphonate Esters, J. of Org. Chem., vol. 57, pp. 873-876, 1992.

Bock et al., Selection of Single-Stranded DNA Molecules That Bind and Inhibit Human Thrombin, Nature, vol. 355, No. 6, pp. 564-566, 1992.

Brenner et al., Encoded Combinatorial Chemistry, Proc. Nat'l. Acad. Sci., vol. 89, pp. 5381-5383, 1992.

Brown et al., NMR Solution Structure of a Peptide Nucleic Acid Complexed with RNA, Science, vol. 265, pp. 777-780, Aug. 1994.

Buchardt et al., Peptide Nucleic Acids and Their Potential Applications in BioTechnology, Trends Biotechnol., vol. 11, pp. 384-386, 1993.

Castanotto et al., Biological and Functional Aspects of Catalytic RNAs, Critical Reviews in Eukaryotic Gene Expression, vol. 2, No. 4, pp. 331-357, 1992.

Dekonig et al., Unconventional Nucleotide Analogues VI, Recueil, vol. 91, pp. 1069-1080, 1971.

Egholm et al., PNA Hybridizes to Complementary Oligonucleotides Obeying the Watson-Crick Hydrogen Bonding Rules, Nature, vol. 365, pp. 566-568, 1993.

Famulok et al., In Vitro Selection of Specific Ligan Binding Nucleic Acids, Agnew. Chem. Int. Ed. Engl, vol. 31, pp. 979-988, 1992.

Famulok et al., In-Vitro Selektion Spezifisch Ligandenbindender Nucleinsaeuren, Agnew: Chem. vol. 104, pp. 1001-1011, 1992.

Freier et al., Modified Oligonucleotides: Hybridization Properties, Pharmacokintic Properties and Pharmacological Activity, J. Cell Biochem Supp.—Keystone Symposium on Ribozymes, Meeting Abstract, A6-017, 1995.

G. Zon, Oligonucleotide Analogues as Potential Chemotherapeutic Agents, Pharmaceutical Research vol. 5, No. 9, pp. 539-549.

(Continued)

*Primary Examiner*—Suryaprabha Chunduru

(57) ABSTRACT

Polyamide-oligonucleotide derivatives of the formula $$F[(DNA\text{-}Li)_q(PNA\text{-}Li)_r(DNA\text{-}Li)_s(PNA)_t]_x F'$$

wherein q, r, s, t are, independently of one another, zero or 1, where the total of two or more adjacent q, r, s and t≧2; x is 1 to 20; DNA is a nucleic acid such as DNA or RNA or a known derivative thereof; Li is a covalent linkage between DNA and PNA, where the covalent linkage comprises a bond or an organic radical with at least one atom from the series consisting of C, N, O or S; PNA is a polyamide structure which contains at least one nucleotide base which is different from thymine; and F and F' are end groups and/or are linked together by a covalent bond, and the physiologically tolerated salts thereof, a process for their preparation and their use as pharmaceutical, as gene probe and as primer, are described.

4 Claims, No Drawings

OTHER PUBLICATIONS

Haralambidis et al., The Synthesis of Polyamide-Oligonucleotide Conjugate Molecules, Nucleic Acids Res. vol. 18, No. 3, pp. 493-499, 1990.

Harvey et al., Antisense and Antigene Properties of Peptide Nucleic Acids, Science, vol. 258, pp. 1481-1485, 1992.

Helene et al., Specific Regulation of Gene Expression by Antisense, Sense and Antigene Nucleic Acids, Biochimica et Biophysica Acta, vol. 1409, pp. 99-125, 1990.

Huang et al., Acyclic Nucleic Acid Analogues, J. Org. Chem, vol. 56, pp. 6007-6018, 1991.

Hyrup et al., Modification of the binding affinity of peptide nucleic acids (PNA). PNA with extended backbones consisting of 2-aminoethyl-alanine or 3-aminopropylglycine units , J. Chem Soc., Chem. Comm., p. 518, 1993.

J.S. Cohen ed., Synthesis of Oligonucleotides and Oligonucleotide Analogues, Antisense Inhibitors of Gene Expression, CRC Press. Boca Raton, FL. pp. 7-24.

JCBN, Nomenclature and Symbolism for Amino Acids and Peptides, Eur. J. Biochem., vol. 138, pp. 9-37, 1984.

Jois et al., Synthesis and Antiviral Evaluation of Some Novel [1,2,4]Triazolo[4,3-b][1,2,4]Triazole Nucleoside Analogs, J. Heterocyclic Chem., vol. 30, pp. 1289-1292, 1993.

Juby et al., Facile Preparation of 3' Oligonucleotide-Peptide Conjugates, Tetrahedron Lett. vol. 32, No. 7, pp. 879-882, 1991.

Koga et al., Alternating .alpha.,.beta.-oligothymidylates with alternating (3'-.3')- and (5'-5')-internucleotidic phosphodiester linkages as models for antisense oligodeoxyribonucleotides , J. of Organic Chemistry, vol. 56, No. 12, pp. 3758-3759.

Lewis, Peptide Analogues of DNA Incorporating Nucleobase-Ala-Pro Subunits, Tetrahedron Letters, vol. 34, No. 36, pp. 5697-5700, 1993.

Matteucci et al., Synthesis of Deoxyoligonucleotides on a Polymer Support, J. Am. Chem. Soc., vol. 103, pp. 3185-3191, 1981.

Mitchell et al., Boron Triffluoride-Methanol Complex as a Nondepurinating Detritylating Agent in DNA Synthesis, Nucleic Acids Research, vol. 18, No. 17, p. 5321, Sep. 1990.

Nielsen et al., Peptide Nucleic Acid (PNA), a DNA Mimic With a Peptide Backbone, Bioconjugate Chem., vol. 5, pp. 3-7, 1994.

Nielsen te al., Sequence-selective recognition of DNA by strand displacement with a thymine substituted polyamide, Science, 1991, vol. 254, pp. 1497-1500.

Pardridge et al., Vector-Mediated Delivery of a Polyamide ("Peptide") Nucleic Acid Analogue Through the Blood-Brain Barrier in Vivo, Proc. Nat'l. Acad. Sci., vol. 92, pp. 5592-5596, 1995.

Peffer et al., Strand-Invasion of Duplex DNA by Peptide Nucleic Acid Oligomers, Proc. Nat'l. Acad. Sci., vol. 90, pp. 10648-10652, 1993.

Renault et al., Synthesis and Antiviral Evaluation of Furopyrimidine Diones Cyclic and Acyclic, Nucleosid Analogues, Heterocycles, vol. 41, No. 5, pp. 937-945, 1995.

Robles et al., Stepwise Solid-Phase Synthesis of the Nucleopeptide Phac-Phe-Val-Ser-(P3 ACT)-Gly OH, J. Org Chem., vol. 59, pp. 2482-2486, 1994.

Rossi et al., RNA Enzymes (Ribozymes) As Antiviral Therapeutic Agents, Tibtech, vol. 8, pp. 179-183, 1990.

Sandkuehler et al., Propriospinal Neurones Are Involved in Descending Inhibition of Lumbar Spinal Dorsal Horn Neurones From the Mid Brain, Proc. of the VIth World Congress on Pain, pp. 313-318, undated.

Tong et al., The Synthesis of Oligonucleotide-Polyamide Conjugate Molecules Suitable as PCR Primers, J. Org. Chem., vol. 58, pp. 2223-2231, 1993.

Uhlmann et al., Antisense Oligonucleotides: A New Therapeutic Principle, Chemical Reviews, vol. 90, No. 4, pp. 544-584, 1990.

Van Der Laan et al., Solid Support Synthesis of a PNA-DNA Hybrid, Recl. Trav. Chim. Pays-Bas vol. 114, pp. 295-297, Jun. 1995.

Verheggen et al., Synthesis and Antiherpes Activity of 1,5-Anhydrohexitol Nucleosides, J. Med. Chem., vol. 36, pp. 2033-2040, Jul. 1993.

Wei et al., Synthesis of Oligoarginine-Oligonucleotide Conjugates and Oligoarginine-Bridged Oligonucleotide Pairs, Bioconjugate Chem., vol. 5, pp. 468-474, 1994.

Wenninger et al., Synthesis and Hybridization Properties of Modified Oligonucleotides with PNA-DNA Dimer Blocks, Nucleosides Nucleotides, vol. 16 (7-9) pp. 977-980, 1997.

* cited by examiner

SEQUENCE LISTING

<160> NUMBER OF SEQ ID NOS: 70

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      PNA

```
<400> SEQUENCE: 1
acacccaatt ctgaaaatgg                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 2
aggtccctgt tcgggcgcca                                              20

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 3
gtcgacaccc aattctgaaa atggataa                                     28

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 4
gctatgtcga cacccaattc tgaaa                                        25

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 5
tcgtcgctgt ctccgcttct tcttcctgcc a                                 31

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 6
gcggggctcc atgggggtcg                                              20

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 7
```
cagctgcaac ccagc                                                        15

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 8
ggctgctgga gcggggcaca c                                                 21

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 9
aacgttgagg ggcat                                                        15

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 10
gtgccggggt cttcgggc                                                     18

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 11
ggagaacatc atggtcgaaa g                                                 21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 12
cccgagaaca tcatggtcga ag                                                22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 13
ggggaaagcc cggcaagggg                                           20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 14
cacccgcctt ggcctcccac                                           20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 15
gggactccgg cgcagcgc                                             18

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 16
ggcaaacttt cttttcctcc                                           20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 17
gggaaggagg aggatgagg                                            19

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 18
ggcagtcatc cagcttcgga g                                         21

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 19
gcagtaagca tccatatc                                             18

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 20
cccccaccac ttcccctctc                                          20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 21
ctcccccacc acttcccctc                                          20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 22
gctgggagcc atagcgagg                                           19

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 23
actgctgcct cttgtctcag g                                        21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 24
caatcaatga cttcaagagt tc                                       22

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 25
gtgtcggggt ctccgggc                                            18

```
<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 26
cacgttgagg ggcat                                                          15

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 27
gtcttccata gttactca                                                       18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 28
gatcaggcgt gcctcaaa                                                       18

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 29
atcgtcgtat t                                                              11

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 30
atcgtcgtat tagtc                                                          15

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 31
ggggtccatg ggggt                                                          15
```

```
<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 32
ggggctccag ggggt                                                     15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 33
cgagacatca ggtcg                                                     15

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 34
cgagacatca tggtcg                                                    16

<210> SEQ ID NO 35
<211> LENGTH: 16
<212> TYPE: DNA
<213> ORGANISM: Artificial Sequence
<220> FEATURE:
<223> OTHER INFORMATION: Description of Combined DNA/RNA Molecule:
      Synthetic PNA

<400> SEQUENCE: 35
cgagaacatc atgucg                                                    16

<210> SEQ ID NO 36
<211> LENGTH: 11
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 36
acatcaggtc g                                                         11

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 37
ataatgtctc g                                                         11

<210> SEQ ID NO 38
```

```
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 38
acatcatggt cg                                                           12

<210> SEQ ID NO 39
<211> LENGTH: 8
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 39 aaaggt cg                                                                8

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 40
taatacgact cacta                                                        15

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 41 tcctcctgc gg                                                            11

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 42
ggggggggtt tttttt                                                       17

<210> SEQ ID NO 43
<211> LENGTH: 14
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 43
atcgtcgtat agtc                                                         14

<210> SEQ ID NO 44
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 44
gactaatacg acgat                                                     15

<210> SEQ ID NO 45
<211> LENGTH: 11
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 45
atcgtcgtat t                                                         11

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 46
atcgtcgtat tagtc                                                     15

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 47
tagcagcata atcag                                                     15

<210> SEQ ID NO 48
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 48
acatcatggt cg                                                        12

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 49
cgaccatgat gt                                                        12

<210> SEQ ID NO 50
<211> LENGTH: 81
<212> TYPE: DNA
```

```
<213> ORGANISM: Artificial Sequence
<220> FEATURE:
<223> OTHER INFORMATION: Description of Artificial Sequence: Synthetic
      PNA

<400> SEQUENCE: 50
gccccaggga gaaggcaact ggaccgaagg cgcttgtgga gaaggagttc atagctgggc    60
tccctatagt gagtcgtatt a                                              81

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 51
taatacgact cactatag                                                  18

<210> SEQ ID NO 52
<211> LENGTH: 13
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 52
ccctctttgt ggg                                                       13

<210> SEQ ID NO 53
<211> LENGTH: 14
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 53
ccctcttaag aggg                                                      14

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 54
tttttttttt ttttt                                                     15

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 55
tttttttttt ttttt                                                     15

<210> SEQ ID NO 56
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 56 ggggggggt ttttt                                                      15

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 57 aaaaaaggg ggggg                                                      15

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 58 ggggggggt ttttt                                                      15

<210> SEQ ID NO 59
<211> LENGTH: 11
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 59
tcctcctgcg g                                                         11

<210> SEQ ID NO 60
<211> LENGTH: 11
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 60
tcctcctgcg g                                                         11

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 61
aaaaaaaaaa gggggggg                                                  18

<210> SEQ ID NO 62
<211> LENGTH: 15
<212> TYPE: DNA
```

```
<213> ORGANISM: Artificial Sequence
<220> FEATURE:
<223> OTHER INFORMATION: Description of Artificial Sequence: Synthetic
      PNA

<400> SEQUENCE: 62
taatacgact cacta                                                    15

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 63
tatccgtcat                                                          10

<210> SEQ ID NO 64
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 64
tatccgtcat                                                          10

<210> SEQ ID NO 65
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 65
atgcggaata                                                          10

<210> SEQ ID NO 66
<211> LENGTH: 10
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 66
atgcggaata                                                          10

<210> SEQ ID NO 67
<211> LENGTH: 15
<212> TYPE: DNA
<213> ORGANISM: Artificial Sequence
<220> FEATURE:
<223> OTHER INFORMATION: Description of Combined DNA/RNA Molecule:
      Synthetic PNA

<400> SEQUENCE: 67
cugauagcat ccatg                                                    15

<210> SEQ ID NO 68
<211> LENGTH: 17
<212> TYPE: DNA
<213> ORGANISM: Artificial Sequence
```

```
<220> FEATURE:
<223> OTHER INFORMATION: Description of Combined DNA/RNA Molecule:
      Synthetic PNA

<400> SEQUENCE: 68
auuuuaguga tgtacaa                                                        17

<210> SEQ ID NO 69
<211> LENGTH: 17
<212> TYPE: DNA
<213> ORGANISM: Artificial Sequence
<220> FEATURE:
<223> OTHER INFORMATION: Description of Combined DNA/RNA Molecule:
      Synthetic PNA

<400> SEQUENCE: 69
ucauggugcc tttgcag                                                        17

<210> SEQ ID NO 70
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 70
ccaacacgac ctgct                                                          15
```

POLYAMIDE-OLIGONUCLEOTIDE DERIVATIVES, THEIR PREPARATION AND USE

CROSS REFERENCE TO RELATED APPLICATIONS

This Application is a divisional of U.S. patent application Ser. No. 09/793,146, filed Feb. 27, 2001 now U.S. Pat. No. 6,919,441, which is a continuation of U.S. patent application Ser. No. 08/982,008, filed Dec. 1, 1997 now abandoned, which is a Continuation-in-Part of U.S application Ser. No. 08/402,838 filed Mar. 13, 1995, now abandoned, priority to both of which is claimed, and the disclosures of which are hereby incorporated.

The present invention relates to novel polyamide-oligonucleotide derivatives with valuable physical, biological and pharmacological properties. Their application relates to use as inhibitors of gene expression (antisense oligonucleotides, ribozymes, sense oligonucleotides and triplex forming oligonucleotides), as probes for detecting nucleic acids and as aids in molecular biology.

Oligonucleotides are finding increasing application as inhibitors of gene expression (G. Zon, Pharmaceutical Research 5, 539 (1988); J. S. Cohen, Topics in Molecular and Structural Biology 12 (1989) Macmillan Press; C. Helene and J. J. Toulme, Biochimica et Biophysica Acta 1049, 99 (1990); E. Uhlmann and A. Peyman, Chemical Reviews 90, 543 (1990)). Antisense oligonucleotides are nucleic acid fragments whose base sequence is complementary to that of an mRNA to be inhibited. This target mRNA can be of cellular, viral or other pathogenic origin. Suitable cellular target sequences are, for example, those of receptors, cell-adhesion proteins, enzymes, immunomodulators, cytokines, growth factors, ion channels or oncogenes. Inhibition of virus replication with the aid of antisense oligonucleotides has been described, for example, for HBV (hepatitis B virus), HSV-1 and -2 (herpes simplex virus type I and II), HIV (human immunodeficiency virus) and influenza viruses. This entails use of oligonucleotides which are complementary to the viral nucleic acid. Sense oligonucleotides are, by contrast, designed to have a sequence such that, for example, they bind ("trap") nucleic acid-binding proteins or nucleic acid-processing enzymes and thus inhibit their biological activity (C. Helene and J. J. Toulme, Biochimica et Biophysica Acta 1049, 99 (1990)). Viral targets which may be mentioned here are, for example, reverse transcriptase, DNA polymerase and transactivator proteins. Triplex-forming oligonucleotides generally have the DNA as target and, after binding thereto, form a triple helix structure. Whereas in general the processing (splicing etc.) of the mRNA or translation thereof into protein is inhibited by antisense oligonucleotides, the transcription or replication of the DNA is inhibited by triplex-forming oligonucleotides (C. Helene and J. J. Toulme, Biochim. Biophys. Acta 1049 (1990) 99-125; E. Uhlmann and A. Peyman, Chemical Reviews 90, 543 (1990)). However, it is also possible to bind single-stranded nucleic acids in a first hybridization with an antisense oligonucleotide to form a double strand, which then in a second hybridization with a triplex-forming oligonucleotide forms a triplex structure. The antisense and triplex binding regions may in this case be accommodated either in two separate oligonucleotides or else in one oligonucleotide. Another application of synthetic oligonucleotides comprises so-called ribozymes which destroy the target RNA as a consequence of their ribonuclease activity (J. J. Rossi and N. Sarver, TIBTECH (1990) 8, 179; Castanetto et al., Critical Rev. Eukar. Gene Expr. (1992) 2, 331).

The compounds according to the invention can also be used in therapy in the sense of aptamers. Aptamers are oligomeric nucleic acids or analogs thereof which bind with high affinity to proteins. The aptamers are found by in vitro selection from a random mixture (Famulok and Szostak (1992) Angew. Chem. 104, 1001-1011) and this has been carried out successfully for a thrombin-binding aptamer (Bock et al. (1992) Nature 355, 564-566). The procedure for this can be such that the base sequence of the aptamer is determined by screening an oligonucleotide mixture, and this base sequence is then transferred to polyamide-oligonucleotide analogs. Another possibility comprises encoding the binding region of the aptamer, to facilitate identification, by a separate non-binding part of the molecule (Brenner and Lerner (1992) PNAS 89, 5381-5383).

In DNA diagnosis, nucleic acid fragments with suitable labeling are used as so-called DNA probes for specific hybridization onto a nucleic acid to be detected. The specific formation of the new double strand is in this case followed with the aid of the labeling, which is preferably non-radioactive. It is possible in this way to detect genetic, malignant or viral diseases or diseases caused by other pathogens.

Oligonucleotides in their naturally occurring form have little or no suitability for most of the said applications. They have to be chemically modified so that they satisfy the specific requirements. For oligonucleotides to be employable in biological systems, for example for inhibition of virus replication, they must meet the following requirements:

1. They must have sufficiently high stability under in vivo conditions, that is to say both in serum and intracellularly.
2. Their properties must be such that they can pass through the cell membrane and nuclear membrane.
3. Under physiological conditions they must bind in a base-specific manner to their target nucleic acid in order to display the inhibitory effect.

Points 1 to 3 are not a requirement for DNA probes; however, these oligonucleotides must be derivatized so that detection is possible, for example by fluorescence, chemiluminescence, colorimetry or specific staining (Beck and Köster, Anal. Chem. 62, 2258 (1990)). The chemical modification of the oligonucleotides usually takes place by appropriate modification of the phosphate backbone, ribose unit or the nucleotide bases (J. S. Cohen, Topics in Molecular and Structural Biology 12 (1989) Macmillan Press; E. Uhlmann and A. Peyman, Chemical Reviews 90, 543 (1990)). Another frequently used method is to prepare oligonucleotide 5' conjugates by reaction of the 5'-hydroxyl group with appropriate phosphorylation reagents. If, on the other hand, all the internucleotide phosphate residues are modified there is often a drastic change in the properties of the oligonucleotides. For example, the solubility of methyl phosphonates in aqueous medium is greatly reduced, while all-phosphorothioate oligonucleotides often act in a non-sequence-specific manner.

There have recently been descriptions of polyamide-nucleic acid derivatives (Michael Egholm, Peter E. Nielsen, Rolf H. Berg and Ole Buchardt, Science 1991, 254, 1497-1500; WO 92/20702; M. Egholm et al. Nature (1993) 365, 566-568; P. Nielsen, (1994) Bioconjugate Chem. 5, 3-7) which bind to complementary target sequences (DNA or RNA) with higher affinity than natural oligonucleotides. These so-called peptide or polyamide nucleic acids (PNA) are DNA-analogous compounds in which the deoxyribose phosphate skeleton has been replaced by a polyamide oligomer. These compounds have the advantage compared with natural oligonucleotides that they are very stable in serum. However, on the other hand, they have the following disadvantageous properties:

(1) The amount taken up in cells is zero or undetectable. However, since antisense or triplex-forming oligonucleotides are able to display their activity only in the cell, the PNAs as such are unsuitable for inhibition of gene expression in vivo.
(2) The PNAs tend to aggregate in aqueous solution, that is to say also under physiological conditions. Their solubility in aqueous buffer is therefore low and they are unavailable for hybridization to complementary sequences.
(3) The PNAs additionally have high affinity for various materials such as ®Sephadex (from Pharmacia) or ®Bond Elut (from Varian) used to purify the oligomers, so that the PNAs can often be isolated only in poor yields.
(4) Another serious disadvantage of the PNAs is that they do not bind in an unambiguous orientation to complementary nucleic acids. The sequence specificity is therefore reduced by comparison with natural oligonucleotides. Whereas natural nucleic acids generally hybridize to complementary nucleic acids in the antiparallel orientation, PNAs may bind both in the antiparallel and in the parallel orientation.
(5) WO 92/20702 mentions an oligonucleotide-PNA conjugate $(T)_7(5'-L-N)(t)_6$-Ala (FIG. 25; substitute sheet), where $(T)_7$ is a natural heptathymidylate oligonucleotide which is linked via its 5'-O-phosphate and 4-hydroxybutyric acid (L) to the primary amino group (N) of a PNA-hexathymidylate $(t)_7$ and alanine (Ala). Neither the synthesis of this compound nor any properties have been described.
(6) PNAs show highly cytotoxic properties in the μmolar range in cell culture experiments.

The orientation of the base-pairing nucleic acid strands is defined as follows: (cf. Egholm et al.; Nature 365 (1993) 566-568).

```
A)
5' ---------- 3'                    DNA  ap Duplex  ap = antiparallel

3' ---------- 5'                    DNA

B)
5' ---------- 3'                    DNA  p Duplex  p = parallel

5' ---------- 3'                    DNA

C)
5' ---------- 3'                    DNA  ap Duplex (DNA · PNA)

C ----------- N                     PNA

D)
5' ---------- 3'                    DNA  p Duplex (DNA · PNA)

N ----------- C                     PNA

E)
C ----------- N                     PNA

5' ---------- 3'                    DNA (Pu) ap · ap triplex (DNA · DNA · PNA)

3' ---------- 5'                    DNA      Pu = purine-rich strand

F)
N ----------- C                     PNA

5' ---------- 3'                    DNA (Pu) ap · p triplex (DNA · DNA · PNA)

3' ---------- 5'                    DNA

G)
N ----------- C                     PNA

5' ---------- 3'                    DNA (Pu) ap · p triplex (PNA · DNA · PNA)

C ----------- N                     PNA

H)
C ----------- N                     PNA

5' ---------- 3'                    DNA (Pu) ap · ap triplex (PNA · DNA · PNA)

C ----------- N'                    PNA

I)
N ----------- C                     PNA
```

```
5' ---------- 3'            DNA (Pu) p · p triplex (DNA · DNA · PNA)

N ---------- C'             PNA

K)

C ---------- N              PNA

5' ---------- 3'            DNA (Pu) p · ap triplex (DNA · DNA · PNA)

N ---------- C              PNA
where 5' means the 5' end of an oligonucleotide,
3' means the 3' end of an oligonucleotide,
N means the amino terminus of a PNA
C means the carboxyl terminus of a PNA.
```

Cases A)-D) are examples of the types of orientation which are possible in principle for the antisense oligomers. Cases E)-F) show possibilities for triplex formation on single-stranded or double-stranded nucleic acids.

It is moreover possible for two of the PNA or DNA single strands to be linked together. For example, in E) the N terminus of the PNA can be linked to the 5' end of the DNA, or in F) the C terminus of the PNA can be linked to the 5' end of the DNA.

The object of the invention therefore was to prepare polyamide-oligonucleotide derivatives in which the abovementioned disadvantages are eliminated.

The invention relates to polyamide-oligonucleotide derivatives of the formula I $$F[(DNA-Li)_q(PNA-Li)_r(DNA-Li)_s(PNA)_t]_xF' \quad (I)$$

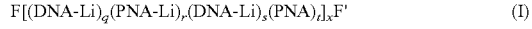

wherein q, r, s, t are, independently of one another, zero or 1, where the total of two or more adjacent q, r, s and t $\geq 2$;
x is 1 to 20, preferably 1 to 5, particularly preferably 1;

DNA is a nucleic acid such as DNA or RNA or a known derivative thereof;

Li is a covalent linkage between DNA and PNA, where the covalent linkage comprises a bond or an organic radical with at least one atom from the series consisting of C, N, O or S;

PNA is a polyamide structure which contains at least one nucleotide base which is different from thymine; and F and F' are end groups and/or are linked together by a covalent bond (cyclic compounds), and the physiologically tolerated salts thereof.

Particular mention may furthermore be made of polyamide-oligonucleotide derivatives of the formula I in which x is 1 and, at the same time, q=r=1 and s=t=zero or
r=s=1 and q=t=zero or
q=r=s=1 and t=zero or
r=s=t=1 and q=zero.

Preferred compounds have the formulae Ia and Ib

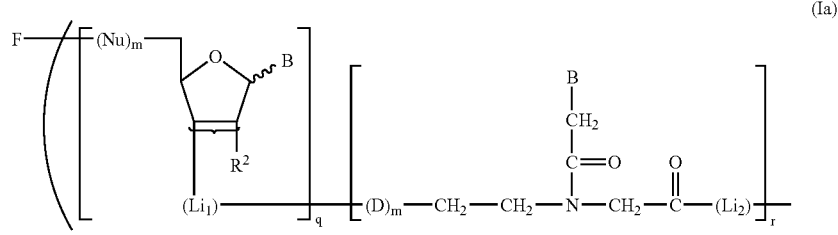

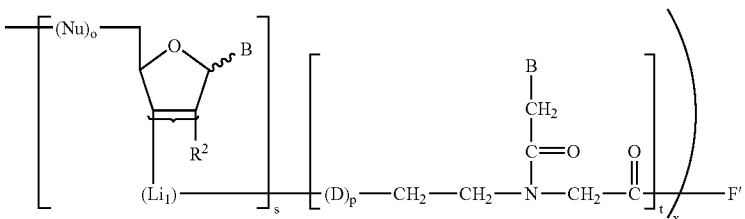

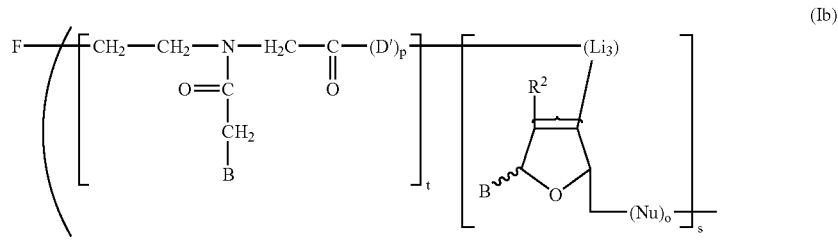

-continued

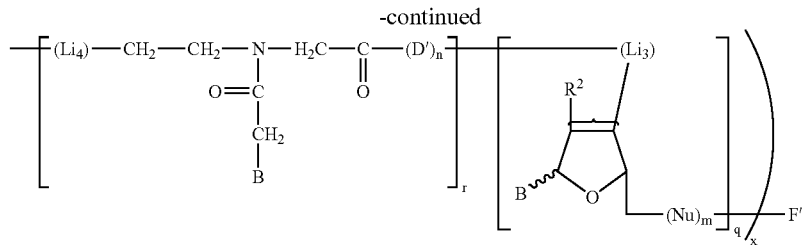

in which
x is 1 to 20, where when x>1 r=s=1 and, at the same time, q=t=zero and o=n=zero to 5;
q, r, s, t are, independently of one another, zero or 1, where the total of two or more adjacent q, r, s and t≧2;
$R^2$ is hydrogen, hydroxyl, $C_1$-$C_{18}$-alkoxy, preferably $C_1$-$C_6$-alkoxy, halogen such as F or Cl, preferably F, azido or amino;
B is, independently of one another, a base customary in nucleotide chemistry, for example natural bases such as adenine, cytosine, thymine, guanine, uracil, inosine or unnatural bases such as, for example, purine, 2,6-diaminopurine, 7-deazaadenine, 7-deazaguanine, $N^4,N^4$-ethanocytosine, $N^6,N^6$-ethano-2,6-diaminopurine, pseudoisocytosine, 5-methylcytosine, 5-fluorouracil, 5-($C_3$-$C_6$)-alkynyluracil, 5-($C_3$-$C_6$)-alkynylcytosine or the prodrug forms thereof, and the "curved bracket" indicates that $R^2$ and the adjacent substituent can be in the 2' position and 3' position or else conversely in the 3' position and 2' position;
Nu is a radical of the formulae IIa or IIb

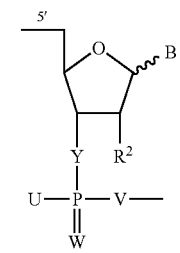 (IIa)

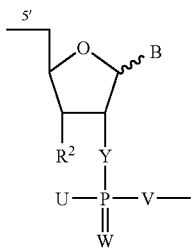 (IIb)

in which
$R^2$ and B are as defined above;
U is hydroxyl, mercapto, $C_1$-$C_{18}$-alkyl, preferably $C_1$-$C_8$-alkyl, $C_1$-$C_{18}$-alkoxy, preferably $C_1$-$C_8$-alkoxy, $C_6$-$C_{20}$-aryl, preferably $C_6$-$C_{12}$-aryl, $C_6$-$C_{14}$-aryl-$C_1$-$C_8$-alkyl, preferably $C_6$-aryl-$C_1$-$C_4$-alkyl, $NHR^3$ or $NR^3R^4$, and
$R^3$ is $C_1$-$C_{18}$-alkyl or $C_1$-$C_4$-alkoxy-$C_1$-$C_4$-alkyl, preferably $C_1$-$C_8$-alkyl or $C_1$-$C_4$-alkoxy-$C_1$-$C_4$-alkyl, particularly preferably $C_1$-$C_4$-alkyl or methoxyethyl and
$R^4$ is $C_1$-$C_{18}$-alkyl, preferably $C_1$-$C_8$-alkyl and particularly preferably $C_1$-$C_4$-alkyl, or $R^3$ and $R^4$ is, together with the nitrogen atom carrying them, a 5-6-membered heterocyclic ring which can additionally contain another hetero atom from the series consisting of O, S, N, such as, for example, morpholine;
V is oxy, thio or imino;
W is oxo or thioxo;
Y is oxy, thio, methylene or imino;
m is zero to 20;
o is zero to 20;
D is a radical of the formula III

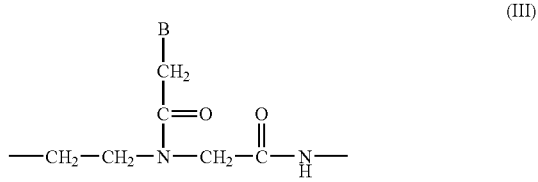 (III)

in which B is as defined above;
D' is a radical of the formula IV

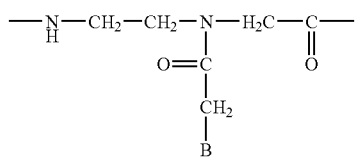 (IV)

in which B is as defined above;
n is zero to 20;
p is zero to 20;
$Li_1$, $Li_2$, $Li_3$ and $Li_4$ are each, independently of one another, a structure of the formula V $$[(V')-(G)-(G')]_\epsilon \qquad (V)$$

where, independently of one another,
$\epsilon$ is 1 to 5, preferably 1-2,
V' is oxygen, NH, a bond or a radical of the formula VI

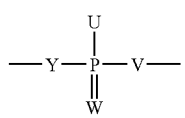 (VI)

in which
U, V, W and Y are as defined above;
G can be $C_1$-$C_{12}$-alkanediyl, preferably $C_1$-$C_6$-alkanediyl, where alkanediyl can optionally be substituted by halogen, preferably F or chlorine, amino, hydroxyl, $C_1$-$C_{18}$-alkyl, preferably $C_1$-$C_6$-alkyl, $C_1$-$C_{18}$-alkoxy, preferably $C_1$-$C_6$-alkoxy, $C_6$-$C_{14}$-aryl, preferably $C_6$-aryl, or $C_6$-$C_{14}$-aryl-$C_1$-$C_{18}$-alkyl, preferably $C_6$-aryl-$C_1$-$C_4$-alkyl; $C_6$-$C_{14}$-aryl-di-$C_1$-$C_{12}$-alkanediyl, preferably $C_6$-aryl-di-$C_1$-$C_4$-alkanediyl, or a group of the formula $(CH_2CH_2O)_\delta CH_2CH_2$ in which $\delta$ can be 1 to 11, preferably 1 to 7; or a bond; and G' is oxy, thio, imino, —C(O)—, —C(O)NH—, a bond or a radical of the formula VI in which U, V, W and Y are as defined above; and F and F' are linked by a bond (cyclic compounds) and/or F is $R^0$—$(A)_k$—V— and F' in formula Ia is -$(Q)_1$-$R^1$ and in formula Ib is $V^1$-$(A)_1$-$R^1$, where $R^0$ is hydrogen, $C_1$-$C_{18}$-alkanoyl, preferably $C_8$-$C_{18}$-alkanoyl, $C_1$-$C_{18}$-alkoxycarbonyl, $C_3$-$C_8$-cycloalkanoyl, $C_7$-$C_{15}$-aroyl, $C_3$-$C_{13}$-heteroaroyl or a group which favors intracellular uptake of the oligomer or serves as labeling of a DNA probe or, in the hybridization of the oligomer onto the target nucleic acid, attacks the latter with binding, crosslinking or cleavage; or if k is zero, $R^0$ is hydrogen or together with V is a radical of the formula VII

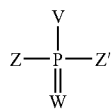

(VII)

in which

Z and Z' are, independently of one another, hydroxyl, mercapto, $C_1$-$C_{22}$-alkoxy, preferably $C_{12}$-$C_{18}$-alkoxy, $C_1$-$C_{18}$-alkyl, preferably $C_{12}$-$C_{18}$-alkyl, $C_6$-$C_{20}$-aryl, preferably $C_6$-$C_{16}$-aryl, $C_6$-$C_{14}$-aryl-$C_1$-$C_{18}$-alkyl, preferably $C_6$-aryl-$C_1$-$C_4$-alkyl, $C_1$-$C_{22}$-alkylthio, preferably $C_{12}$-$C_{18}$-alkylthio, $NHR^3$, $NR^3R^4$, or a group which favors intracellular uptake of the oligomer or serves as labeling of a DNA probe or, in the hybridization of the oligomer onto the target nucleic acid, attacks the latter with binding, crosslinking or cleavage, and in which $R^3$, $R^4$, V and W are as defined above;

$R^1$ is hydrogen or $Q^o$ where $R^1$ is always only hydrogen when at the same time 1 is zero and in formula Ia t is zero and s is 1 and $Li_1$ is a structure of the formula V with V'=bond, G=bond, $\epsilon$=1 and G'=oxy, thio, imino or a radical of the formula VI with U=Z or in formula Ib q is 1 or q=r=zero and in F'=$V^1$-$(A)_1$-$R^1$ with $V^1$=V, A and Q are, independently of one another, the residue of a natural or unnatural amino acid, preferably from the series consisting of glycine, leucine, histidine, phenylalanine, cysteine, lysine, arginine, aspartic acid, glutamic acid, proline, tetrahydroisoquinoline-3-carboxylic acid, octahydroindole-2-carboxylic acid, N-(2-aminoethyl) glycine;

$Q^o$ is hydroxyl, OR', $NH_2$, NHR" with

R'=$C_1$-$C_{18}$-alkyl, preferably $C_{12}$-$C_{18}$-alkyl and R"=$C_1$-$C_{18}$-alkyl, preferably $C_{12}$-$C_{18}$-alkyl, $C_1$-$C_{18}$-aminoalkyl, preferably $C_{12}$-$C_{18}$-aminoalkyl, $C_1$-$C_{18}$-hydroxyalkyl, preferably $C_{12}$-$C_{18}$-hydroxyalkyl;

V is as defined above;

$V^1$ is a bond or V, where in F' only in formula Ib with q=zero and r=1 $V^1$ is always a bond;

k is zero to 10;

l is zero to 10;

with the proviso that a) if in the compound of the formula Ia t is zero and s is 1, and $Li_1$ is (V')-(G)-(G') with V'=a compound of the formula VI, G=$C_2$-$C_{12}$-alkylene and G'=CO, in F'=-$(Q)_1$-$R^1$ l is zero to 10 and $R^1$ is $Q^o$;

b) if in the compound of the formula Ia s=t=zero, $Li_2$ is a bond;

c) if in the compound of the formula Ib t is zero and s is 1, $Li_3$ is a bond;

d) if in the compound of the formula Ib s=t=zero, $Li_4$ is a bond;

where each nucleotide can be in its D or L configuration, and the base can be in the $\alpha$ or $\beta$ position.

Particularly preferred compounds of the formula Ia and Ib are those in which the base is located on the sugar in the $\beta$ position, x is 1 and q=r=1, s=t=zero or r=s=1, q=t=zero or q=r=s=1, t=zero or r=s=t=1, q=zero.

Especially preferred oligomers have the formulae Ia and Ib in which V', V, Y and W have the meaning of thio, oxy, oxo or hydroxyl; these are very particularly preferred if, in addition, $R^2$ is hydrogen.

Also especially preferred are oligomers of the formulae Ia and Ib with $\epsilon$=1, in which $Li_1$, $Li_4$ are a) a compound of the formula V in which V'=oxygen or compound of the formula VI, G=$C_1$-$C_{10}$-alkylene, G'=—CONH—)

b) a compound of the formula V in which G, V' is a bond and G' is a compound of the formula VI with, preferably, U=V=W=Y=oxygen or U=W=Y=oxygen and V=imino $Li_2$, $Li_3$ are a) a compound of the formula V with V'=imino, G=$C_1$-$C_{10}$-alkylene and G'=compound of the formula VI b) a compound of the formula V with V'=imino, G and G'=bond c) a compound of the formula V with V'=imino, G=$C_1$-$C_{10}$-alkylene and G'=V with, preferably, U=V=W=Y=oxygen.

Very particularly preferred oligomers have the formulae Ia and Ib in which V', V, Y and W have the meaning of thio, oxy, oxo or hydroxyl, $R^2$ is hydrogen, $Li_1$ has the meaning of —V'—$[CH_2]_n$C(O)NH— with V'=compound of the formula VI with U=V=W=Y=oxygen or $Li_2$ has the meaning of —HN—$[CH_2]_n$(G')-, where n is 2 to 5 and G' has the formula VI with U, V, W and Y=oxygen.

Additionally preferred oligomers of the formulae Ia and Ib are those in which V', V, Y and W have the meaning of thio, oxy, oxo or hydroxyl, $R^2$ is hydrogen, $Li_1$ has the meaning of —O—$[CH_2]_n$C(O)NH— or $Li_2$ has the meaning of —HN—$[CH_2]_n$(G')-, where n is 2 to 5 and G' has the formula VI with U, V, W and Y=oxygen, and q=zero and r=s=t=1.

Additionally preferred are oligomers of the formulae Ia and Ib in which the curved bracket means that $R^2$ is in the 3' position (see formula IIb). The preferred base in this case is adenine.

The invention is not confined to $\alpha$- and $\beta$-D- and L-ribofuranosides, $\alpha$- and $\beta$-D- and L-deoxyribofuranosides and corresponding carbocyclic five-membered ring analogs but also applies to oligonucleotide analogs which are composed of different sugar building blocks, for example ring-expanded and ring-contracted sugars, acyclic, ring-bridged or other suitable types of sugar derivatives. The invention is furthermore not confined to the derivatives, indicated by way of example in formula I, of the phosphate residue but also relates to known dephospho derivatives.

The oligonucleotide part (DNA in formula I) can therefore be modified from the natural structure in a wide variety of ways. Examples of such modifications, which are introduced by methods known per se, are:

a) Modifications of the phosphate bridge

Examples which may be mentioned are: phosphorothioates, phosphorodithioates, methylphosphonates, phosphoramidates, boranophosphates, phosphate methyl esters, phosphate ethyl esters, phenylphosphonates. Preferred modifications of the phosphate bridge are phosphorothioates, phosphorodithioates and methylphosphonates.

b) Replacement of the phosphate bridge

Examples which may be mentioned are: replacement by formacetal, 3'-thioformacetal, methylhydroxylamine, oxime, methylenedimethylhydrazo, dimethylene sulfone, silyl groups. Replacement by formacetals and 3'-thioformacetals is preferred.

c) Modifications of the sugar

Examples which may be mentioned are: α-anomeric sugars, 2'-O-methylribose, 2'-O-butylribose, 2'-O-allylribose, 2'-fluoro-2"-deoxyribose, 2'-amino-2'-deoxyribose, α-arabinofuranose, carbocyclic sugar analogs. The preferred modification is that by 2'-O-methylribose and 2'-O-n-butylribose.

d) Modifications of the bases with do not alter the specificity of the Watson-Crick base pairing Examples which may be mentioned are: 5-propynyl-2'-deoxyuridine, s-propynyl-2'-deoxycytidine, 5-hexynyl-2'-deoxyuridine, 5-hexynyl-2'-deoxycytidine, 5-fluoro-2'-deoxycytidine, 5-fluoro-2'-deoxyuridine, 5-hydroxymethyl-2'-deoxyuridine, 5-methyl-2'-deoxycytidine, 5-bromo-2'-deoxycytidine. Preferred modifications are 5-propynyl-2'-deoxyuridine, 5-hexynyl-2'-deoxyuridine, 5-hexynyl-2'-deoxycytidine and 5-propynyl-2'-deoxycytidine.

e) 3'-3' and 5'-5' inversions [for example M. Koga et al., J. Org. Chem. 56 (1991) 3757]

f) 5'- and 3'-phosphates, and 5'- and 3'-thiophosphates.

Examples of groups which favor intracellular uptake are various lipophilic radicals such as —O—$(CH_2)_x$—$CH_3$ in which x is an integer from 6 to 18, —O—$(CH_2)_n$—CH=CH—$(CH_2)_m$—$CH_3$ in which n and m are, independently of one another, an integer from 6 to 12, —O—$(CH_2CH_2O)_4$—$(CH_2)_9$—$CH_3$, —O—$(CH_2CH_2O)_8$—$(CH_2)_{13}$—$CH_3$ and —O—$(CH_2CH_2O)_7$—$(CH_2)_{15}$—$CH_3$, but also steroid residues such as cholesteryl or vitamin residues such as vitamin E, vitamin A or vitamin D and other conjugates which utilize natural carrier systems such as bile acid, folic acid, 2-(N-alkyl-N-alkoxyamino)-anthraquinone and conjugates of mannose and peptides of the appropriate receptors which lead to receptor-mediated endocytosis of the oligonucleotides, such as EGF (Epidermal Growth Factor), bradykinin and PDGF (Platelet Derived Growth Factor). By labeling groups are meant fluorescent groups, for example of dansyl (=1-dimethylaminonaphthalene-5-sulfonyl), fluorescein or coumarin derivatives or chemiluminescent groups, for example of acridine derivatives, and the digoxigenin system detectable by ELISA, the biotin group detectable by the biotin/avidin system or else linker arms with functional groups which permit subsequent derivatization with detectable reporter groups, for example an aminoalkyl linker which is reacted with an acridinium active ester to give the chemiluminescence probe. Typical labeling groups are:

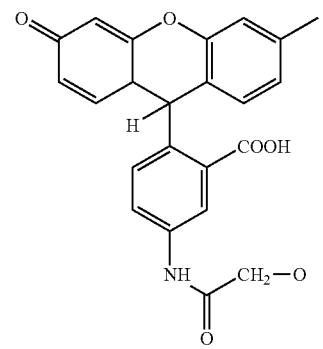

Fluorescein derivative

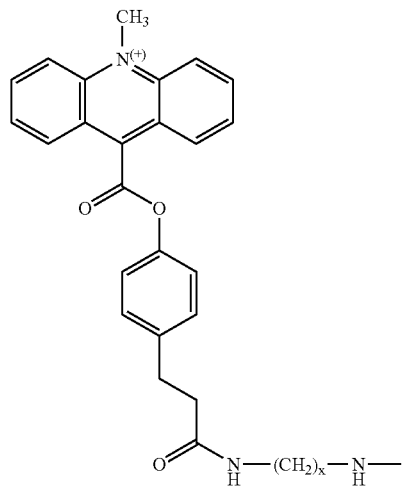

Acridinium ester

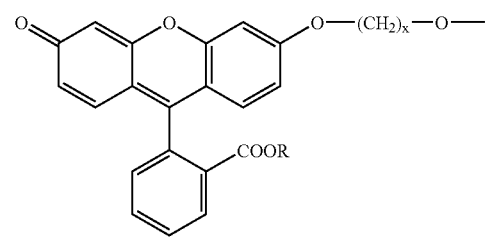

Fluorescein derivative
x = 2-18, preferably 4
R = H or $C_1$-$C_4$-alkyl
(= "Fluorescein" for x = 4 and R = $CH_3$)

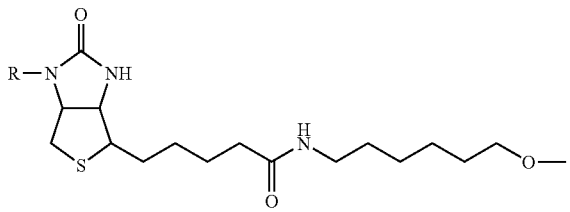

Biotin conjugate
R = H or amino protective group
(= "Biotin" for R = Fmoc)

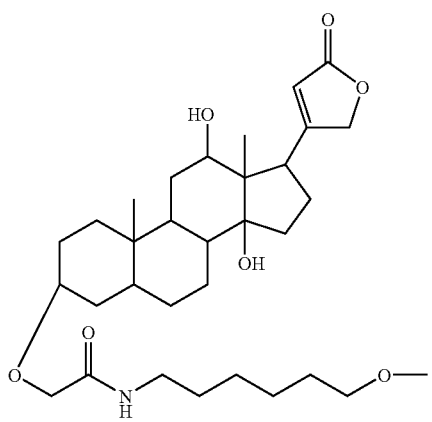

Digoxigenin conjugate

Oligonucleotide analogs which bind to or intercalate and/or cleave or crosslink nucleic acids contain, for example, acridine, psoralen, phenanthridine, naphthoquinone, daunomycin or chloroethylaminoaryl conjugates. Typical intercalating and crosslinking radicals are:

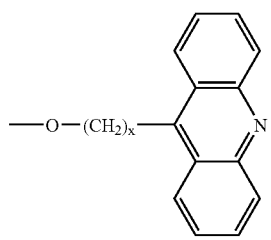

Acridine derivative
x = 2-12, preferably 4

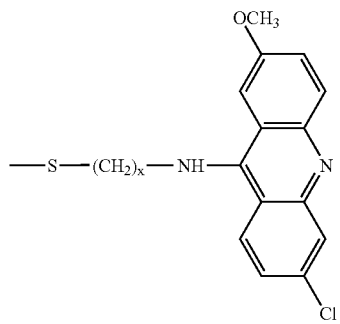

x = 2-12, preferably 4

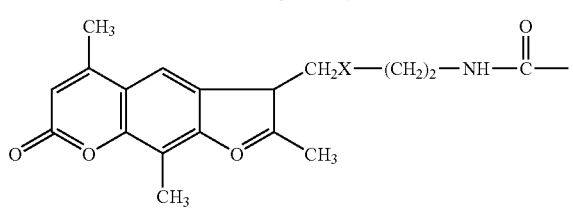

Trimethylpsorolene conjugate
X = —NH— or —O—
(= "psoralene" for x = 0)

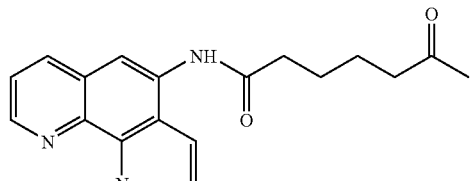

Phenanthroline conjugate

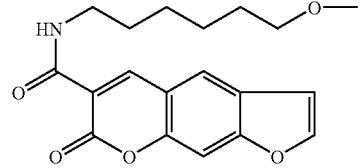

Psoralen conjugate

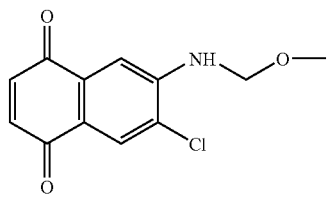

Naphthoquinone conjugate

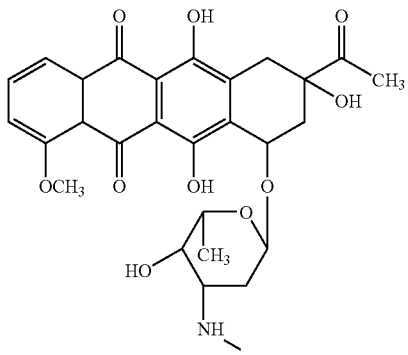

Daunomycin derivative

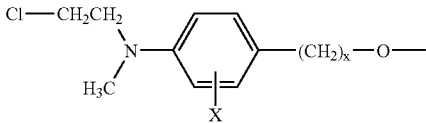

x = 1-18, X = Alkyl, Halogen, $NO_2$, CN, —C(=O)—R

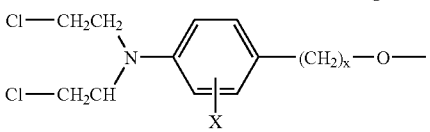

x = 1-18, X = Alkyl, Halogen, $NO_2$, CN, —C(=O)—R

Examples which may be mentioned of $NR^3R^4$ groups in which $R^3$ and $R^4$ form, together with the nitrogen atom carrying them, a 5- to 6-membered heterocyclic ring which additionally contains another hetero atom are the morpholinyl and the imidazolidinyl radical.

The polyamide part (PNA in formula I) is composed of amide structures which contain at least one nucleotide base which is different from thymine. Polyamide structures of this type are composed, for example, of the following building blocks a) to h), preferably a), in which f is 1 to 4, preferably 1 or 2 and g is zero to 3, preferably zero to 2:

a)

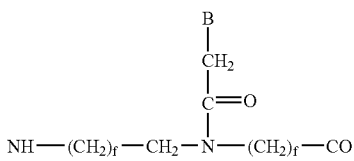

Hyrup et al.; J. Chem. Soc. Chem. Comm. 1993, 519 b)

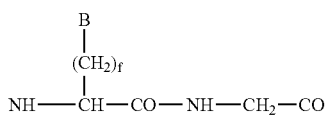

De Konig et al. (1971) Rec. Trav. Chim. 91, 1069 c)

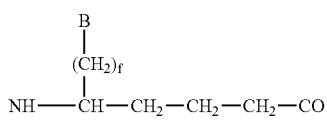

Huang et al. (1991) J. Org. Chem. 56, 6007 d)

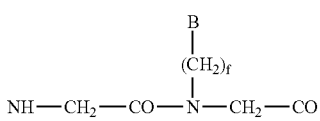

Almarsson et al. (1993) Proc. Natl. Acad. Sci. U.S.A. 90, 7518 e)

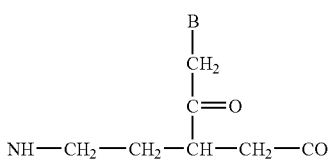

Froehler et al. (1991) WO 93/10820 f)

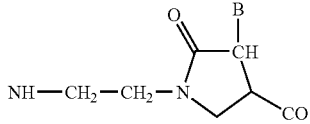

Froehler et al. (1991) WO 93/10820 g)

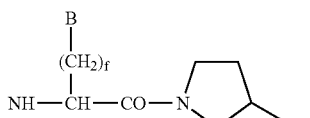

Lewis (1993) Tetrahedron Lett. 34, 5697.

h)

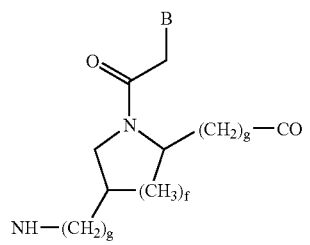

End groups for PNAs are described in the applications, filed simultaneously, with the titles "PNA synthesis using an amino protective group which is labile to weak acids" (HOE 94/F 060, DE-P 44 08 531.1) and "PNA synthesis using a base-labile amino protective group" (HOE 94/F 059, DE-P 44 08 533.8).

Preferred polyamide structures are composed of structures according to a). The latter are particularly preferred when f is 1.

The preparation of polyamide-oligonucleotide derivatives of the formula I takes place similarly to the synthesis of oligonucleotides in solution or, preferably, on solid phase, where appropriate with the assistance of an automatic synthesizer. The oligomer of the formula I can be assembled stepwise by successive condensation of one PNA unit or DNA unit with in each case one nucleotide base onto an appropriately derivatized support or onto a growing oligomer chain. However, the assembly can also take place in fragment fashion, in which case the fragments are first synthesized as polyamide or oligonucleotide structures which are then linked to give the polyamide-oligonucleotide of the formula I. However, it is also possible to use building blocks composed of PNA and nucleotide preferably diners, which are then assembled by the methods of nucleotide chemistry or peptide chemistry to give polyamide-oligonucleotide derivatives.

The assembly of the oligonucleotide part takes place by processes known to the skilled worker, such as the triester method, the H-phosphonate method or phosphoramidite method, preferably by the standard phosphoramidite chemistry of Caruthers (M. D. Matteucci and M. H. Caruthers, J.

Am. Chem. Soc. 103, 3185 (1981)). The polyamide part can be synthesized by the methods of peptide chemistry known to the skilled worker. If the oligonucleotide part and polyamide part are not separately synthesized and subsequently linked, the processes used to assemble the oligonucleotide structure and polyamide structure must be mutually compatible, in which connection a preferred embodiment of the synthesis of the polyamide part is described in the simultaneously filed application with the title "PNA synthesis using an amino protective group which is labile to weak acids" (HOE 94/F 060, DE-P 44 08 531.1).

Depending on whether q, r, s and t are 1 or zero, the synthesis starts with the oligonucleotide part or with the polyamide part. The synthesis of compounds of the formula I whose oligonucleotide part is modified at the 3' and/or at the 5' end takes place in respect of these modifications by the processes described in EP-A 0 552 766 (HOE 92/F 012) (compare synthetic scheme for DNA). The synthesis of compounds of the formula I takes place in respect of the polyamide part by the process described in the simultaneously filed application with the title "PNA synthesis using an amino protective group which is labile to weak acids (HOE 94/F 060, DE-P 44 08 531.1) (compare synthetic scheme for PNA).

Synthetic scheme for DNA
[anchor group]-[polymer]
1. ↓ coupling on of PG-(Nu')-active PG-(Nu')-[anchor group]-[polymer]
2. ↓ elimination of protective group PG H-(Nu')-[anchor group]-[polymer]
3. ↓ repetition of steps 1 and 2 (n-1) times H-(Nu')$_n$-[anchor group]-[polymer]
4. ↓ coupling on of R$^0$-V-active R$^0$-V-(Nu')$_n$-[anchor group]-[polymer]
5. ↓ elimination of polymer and protective groups R$^0$-V-(Nu)$_n$ Synthetic scheme for PNA
[anchor group]-[polymer]
1. ↓ coupling on of PG-(Q')-OH PG-(Q')-[anchor group]-[polymer]
2. ↓ elimination of protective group PG H-(Q')-[anchor group]-[polymer]
3. ↓ repetition of steps 1 and 2 (1-1) times H-(Q')$_l$-[anchor group]-[polymer]
4. ↓ coupling on of PG-[B'/X]—OH PG-[B'/X]-(Q')$_l$-[anchor group]-[polymer]
5. ↓ elimination of protective group PG H-[B'/X]-(Q')$_l$-[anchor group]-[polymer]
6. ↓ repetition of steps 4 and 5 (n-1) times H-[B'/X]$_n$-(Q')$_l$-[anchor group]-[polymer]
7. ↓ coupling on of PG-(A')-OH PG-(A')-[B'/X]$_n$-(Q')$_l$-[anchor group]-[polymer]
8. ↓ elimination of protective group PG H-(A')-[B'/X]$_n$-(Q')$_l$-[anchor group]-[polymer]
9. ↓ repetition of steps 7 and 8 (k-1) times H-(A')$_k$-[B'/X]$_n$-(Q')$_l$-[anchor group]-[polymer]
10. ↓ coupling on of the group R$^0$ R$^0$-(A')$_k$-[B'/X]$_n$-(Q')$_l$-[anchor group]-[polymer]
11. ↓ elimination of polymer and protective groups R$^0$-(A)$_k$-[B/X]$_n$—(Q)$_l$-Q$^o$ The meanings in this are:
PG protective group, preferably a protective group labile to weak acid;
Nu' nucleotide unit whose exocyclic amino group is protected by a suitable protective group;
Nu'-active an activated derivative customary in nucleotide chemistry, such as, for example, of a phosphoramidite, a phosphodiester or an H-phosphonate;
A', B' and Q' are the forms of A, B and Q which are protected where appropriate.

Synthetic scheme for PNA/DNA hybrids of the formula I $$F[(DNA-Li)_q(PNA-Li)_r(DNA-Li)_s(PNA)_t]_xF'$$  (I)

For q=r=s=t=1 and x=1, the following outline of the synthesis applies:
1. ↓ synthesis of the end group F'; where appropriate conjugation to polymer PG-F'
2. ↓ elimination of protective group PG H—F'
3. ↓ conjugation of the polyamide structure PNA-F'
4. ↓ coupling on of a linker Li-PNA-F'
5. ↓ conjugation of the nucleotide structure DNA-Li-PNA-F'
6. ↓ coupling on of a linker Li-DNA-Li-PNA-F'
7. ↓ repetition of steps 3 to 5 DNA-Li-PNA-Li-DNA-Li-PNA-F'
8. ↓ coupling on of the end group F F-DNA-Li-PNA-Li-DNA-Li-PNA-F'

The coupling on of the linker building block can be omitted if appropriate junctions are present in the PNA or DNA building blocks.

For clarification, a synthetic scheme for PNA/DNA hybrids of the formula I is shown and explains by way of example the preparation of a hybrid oligomer in which q=r=s=t=1 and x=1. Initially, the end group F is synthesized by known processes and, in the case of solid-phase synthesis, coupled to a polymeric support (step 1). After elimination of the protective group PG (step 2), which preferably takes place in weakly acidic medium, the polyamide building blocks are coupled on to the desired length of the PNA part (step 3). As junction to the DNA part it is now possible to attach a linker unit (step 4). The conjugation of the nucleotide structure then takes place by successive condensation on of the nucleotide building blocks (step 5), preferably by the known phosphoramidite method. After a linker which makes it possible to join DNA to PNA has been condensed on (step 6), in turn a polyamide structure is assembled. Introduction of a linker which makes it possible to join PNA to DNA, conjugation of another DNA structure (step 7) and final coupling on of the end group F (step 8) result in the hybrid molecule [F-DNA-Li-PNA-Li-DNA-Li-PNA-F']. The linker building blocks can in this case also contain nucleotide bases. To synthesize a hybrid F-DNA-Li-PNA-Li-F' (q=r=1, s=t=zero), for example first steps 1-5 are carried out and then the synthesis is completed with step 8.

To synthesize a hybrid F-PNA-Li-DNA-F' (r=s=1, q=t=zero), for example first steps 1-2 are carried out, then steps 5-6 follow, followed by step 3 and completion of the synthesis with step 8.

To synthesize a hybrid F-PNA-Li-DNA-Li-PNA-F' (r=s=t=1, q=zero), the synthesis starts with steps 1-6. After repetition of step 3, the synthesis is completed with step 8.

If x in formula I is >1, then steps 2-7 must be repeated where appropriate. After assembly of the polymeric chains, the PNA/DNA hybrids must in the case of solid-phase synthesis be cleaved off the support and, where appropriate, the protective groups on the bases, aminoacid side chains and end groups must be eliminated.

However, the PNA part and DNA part can also be synthesized separately by known methods and subsequently coupled together via appropriate activation of at least one component. Activation of the PNA part preferably takes place via the carboxylic acid group, for example as active ester or isothiocyanate, which are then reacted with reactive groups in the DNA part, preferably an amino group. Activation of the DNA part takes place, for example, in the form of a cyanogen bromide condensation known per se, in which the activated phosphate functionality is reacted with a reactive group in the PNA part, preferably an amino group.

It has been found, surprisingly, that the oligomers of the formula Ia and Ib have a greatly increased cellular uptake by comparison with pure PNAs. This improved cellular uptake is very crucial because antisense- or triplex-forming oligomers are able to act only if they are efficiently taken up by cells. Their hybridization behavior is likewise more favorable than in the case of pure PNAS because they preferentially lead to antiparallel duplex formation. Compared with normal oligonucleotides, they have an improved nuclease stability, which is expressed by an increased biological activity. The binding affinity to complementary nucleic acids is better than the other nuclease-stable oligonucleotides such as, for example, phosphorothioates or methylphosphonates. The binding affinity of the compounds according to the invention is at least equally good, but usually better, by comparison with natural oligonucleotides, which are rapidly degraded under serum conditions. The increase in the binding affinity depends on the length of the PNA part. Pure PNAs showed a potent cytotoxic effect at concentrations >5 µM in cell-culture experiments, whereas the compounds according to the invention did not damage the cells. It has furthermore been found that compounds of the formula I inhibit, depending on the base sequence of the PNA part and DNA part, the expression of specific genes, for example of enzymes, receptors or growth factors, in cell culture and in selected examples in animal models.

Further advantages of the PNA/DNA oligomers and PNA/RNA oligomers comprise the possibility of stimulating cellular endonucleases such as, for example, RNase H and RNase L. In contrast to PNAs, the PNA-DNA chimeras according to the invention which have some deoxyribonucleotide units are able, after binding to the complementary target RNA, to cleave the latter in a sequence-specific manner owing to induction of cellular RNase H. A particular embodiment of the oligomers according to the invention furthermore comprises those which are composed of PNA part and a 2',5'-linked oligoadenylate part, preferably tetraadenylate or its cordycepin analog, and which activate cellular RNase L.

The present invention extends very generally to the use of compounds of the formula I as therapeutically active ingredients of a pharmaceutical. By therapeutically active polyamide-oligonucleotide derivatives is meant in general antisense oligonucleotides, triple helix-forming oligonucleotides, aptamers or ribozymes, especially antisense oligonucleotides.

The pharmaceuticals of the present invention can be used, for example, to treat diseases caused by viruses, for example by HIV, HSV-1, HSV-2, influenza, VSV, hepatitis B or papilloma viruses.

Antisense polyamide-oligonucleotide derivatives according to the invention which are active against such targets have, for example, the following base sequence. The length and position of the PNA part and DNA part in these sequences can be altered appropriately to achieve optimal properties.

a) against HIV, for example

5'-A C A C C C A A T T C T G A A A A T     (I)

G G-3' or

5'-A G G T C C C T G T T C G G G C G     (II)

C C A-3' or

5'-G T C G A C A C C C A A T T C T G A A A A     (III)

T G G A T A A-3' or

5'-G C T A T G T C G A C A C C C A A T T C T     (IV)

G A A A-3' or

5'-T C G T C G C T G T C T C C G C T T C T T     (VI)

C T T C C T G C C A or b) against HSV-1, for example

5'-G C G G G G C T C C A T G G G G     (VII)

T C G-3'

The pharmaceuticals of the present invention are also suitable, for example, for the treatment of cancer. In this connection, it is possible to use, for example, polyamide-oligonucleotide sequences which are directed against targets which are responsible for the development of cancer or the growth of cancers. Examples of such targets are:

1) nuclear oncoproteins such as, for example, c-myc, N-myc, c-myb, c-fos, c-fos/jun, PCNA, p120
2) cytoplasmic/membrane-associated oncoproteins such as, for example, EJ-ras, c-Ha-ras, N-ras, rrg, bcl-2, cdc-2, c-raf-1, c-mos, c-src, c-abl
3) cellular receptors such as, for example, the EGF receptor, c-erbA, retinoid receptors, protein kinase regulatory subunit, c-fms
4) cytokines, growth factors, extracellular matrix such as, for example, CSF-1, IL-6, IL-1a, IL-1b, IL-2, IL-4, bFGF, myeloblastin, fibronectin.

Antisense polyamide-oligonucleotides of the formula I according to the invention which are active against such targets have, for example, the following base sequence:

a) against c-Ha-ras, for example

5'-C A G C T G C A A C C C A G C-3'     (VIII)

c) c-myc, for example

5'-G G C T G C T G G A G C G G G G C A     (IX)

C A C-3'

5'-A A C G T T G A G G G G C A T-3'     (X)

d) c-myb, for example

5'-G T G C C G G G G T C T T C G G G C-3'     (XI)

e) c-fos, for example

5'-G G A G A A C A T C A T G G T C G A     (XII)

A A G-3'

5'-C C C G A G A A C A T C A T G G T C G     (XIII)

```
                    -continued
A A G-3'

5'-G G G G A A A G C C C G G C A A G       (XIV)

G G G-3'
``` f) p120, for example

```
5'-C A C C G C C T T G G C C T C C C A C-3'    (XV)
``` g) EGF receptor, for example

```
5'-G G G A C T C C G G C G C A G C G C-3'    (XVI)

5'-G G C A A A C T T T C T T T T C C    (XVII)

T C C-3'
``` h) p53 tumor suppressor, for example

```
5'-G G G A A G G A G G A G G A T G      (XVIII)

A G G-3'

5'-G G C A G T C A T C C A G C T T C G     (XIX)

G A G-3'r
```

The pharmaceuticals of the present invention are furthermore suitable, for example, for the treatment of diseases which are influenced by integrins or cell-cell adhesion receptors, for example by VLA-4, VLA-2, ICAM, VCAM or ELAM.

Antisense polyamide-oligonucleotide derivatives according to the invention which are active against such targets have, for example, the following base sequence:

a) VLA-4, for example

```
5'-G C A G T A A G C A T C C A T A T C-3'    (XX)
or
``` b) ICAM, for example

```
5'-C C C C A C C A C T T C C C T C T    (XXI)

C-3'

5'-C T C C C C A C C A C T T C C C T    (XXII)

C-3'

5'-G C T G G G A G C C A T A G C G A G    (XXIII)

G-3'
``` c) ELAM-1, for example

```
5'-A C T G C T G C C T C T T G T C T C A G    (XXIV)

G-3'

5'-C A A T C A A T G A C T T C A A G A G T T    (XXV)

C-3'
```

The pharmaceuticals of the present invention are also suitable, for example, for preventing restenosis. In this connection, examples of polyamide-oligonucleotide sequences which can be used are those directed against targets which are responsible for proliferation or migration. Examples of such targets are:

1) nuclear transactivator proteins and cyclins such as, for example, c-myc, c-myb, c-fos, c-fos/jun, cyclins and cdc2 kinase
2) mitogens or growth factors such as, for example, PDGF, bFGF, EGF, HB-EGF and TGF-β
3) cellular receptors such as, for example, bFGF receptor, EGF receptor and PDGF receptor.

Antisense polyamide-oligonucleotides according to the invention of the formula I which are active against such targets have, for example, the following base sequence:

a) c-myb

```
5'-G T G T C G G G T C T C C G G G C-3'     (XXVI)
``` b) c-myc

```
5'-C A C G T T G A G G G G C A T-3'
    (XXVII)
``` c) cdc2 kinase

```
5'-G T C T T C C A T A G T T A C T C A-3'
    (XXVIII)
``` d) PCNA (proliferating cell nuclear antigen of rat)

```
5'-G A T C A G G C G T G C C T C A A A-3'    (XXIX)
```

The pharmaceuticals can be used, for example, in the form of pharmaceutical products which can be administered orally, for example in the form of tablets, coated tablets, hard or soft gelatin capsules, solutions, emulsions or suspensions. Inclusion of the pharmaceuticals in liposomes, which optionally contain further components such as proteins, is a likewise suitable administration form. They can also be administered rectally, for example in the form of suppositories, or parenterally, for example in the form of injection solutions. To produce pharmaceutical products, these compounds can be processed in therapeutically inert organic and inorganic excipients. Examples of such excipients for tablets, coated tablets and hard gelatin capsules are lactose, corn starch or derivatives thereof, talc and stearic acid or salts thereof. Suitable excipients for producing solutions are water, polyols, sucrose, invert sugar and glucose. Suitable excipients for injection solutions are water, alcohols, polyols, glycerol and vegetable oils. Suitable excipients for suppositories are vegetable and hardened oils, waxes, fats and semiliquid polyols. The pharmaceutical products may also contain preservatives, solvents, stabilizers, wetting agents, emulsifiers, sweeteners, colorants, flavorings, salts to alter the osmotic pressure, buffers, coating agents, antioxidants and, where appropriate, other therapeutic active substances.

Preferred administration forms are topical applications, local applications such as, for example, with the aid of a catheter or else injections. For injection, the antisense polyamide-oligonucleotide derivatives are formulated in a liquid solution, preferably in a physiologically acceptable buffer such as, for example, Hank's solution or Ringer's solution. The antisense polyamideoligonucleotides can, however, also be formulated in solid form and be dissolved or suspended before use. The dosages preferred for systemic administration are about 0.01 mg/kg to about 50 mg/kg of body weight and day.

The invention extends very generally to the use of compounds of the formula I as DNA probes or primers in DNA diagnosis, in particular in the sense of the gene probes mentioned in HOE 92/F 406 (EP-A 0 602 524), and generally as aids in molecular biology.

Gene probes, also called DNA probes or hybridization probes, play a large part in DNA diagnosis for sequence-specific detection of particular genes. A gene probe is generally composed of a recognition sequence and of a suitable labeling group (label). The specificity of the determination of a target sequence in an analytical sample by hybridization with a complementary gene probe is determined by the recognition sequence and its chemical structure. The PNAs have the advantage, compared with oligonucleotides of natural structure, that they have a higher affinity for the target sequence. However, the specificity of the hybridization is reduced because PNAs, in contrast to natural DNA, are able to bind both in parallel and in antiparallel orientation to single-stranded nucleic acids. The PNA/DNA oligomers according to the invention likewise show an increased binding affinity but very preferentially bind in the desired antiparallel orientation.

It is moreover possible, by appropriate selection of the PNA part and DNA part in a gene probe, to have a beneficial effect on the differentiation capacity because base mispairing in the PNA part leads to a greater depression of the melting temperature of a hybrid than does a base mispairing in the DNA part. This is particularly important with regard to differentiation in the case of point mutations as occur, for example, in the transition from protooncogenes into the corresponding oncogenes (pathogenic state). The advantage of the better discrimination between pathogenic and non-pathogenic state can also be utilized in the form of the primer property of the PNA/DNA oligomers according to the invention as long as these have a free 3'-hydroxyl group in the DNA part. PNAs as such have no primer function for polymerases. It has been found, surprisingly, that even one nucleoside unit at the end of a PNA/DNA oligomer is sufficient to initiate the DNA polymerase reaction, for example with DNA polymerase (Klenow fragment). Various polymerases can be employed depending on the characteristics of the PNA/DNA primer and the nature of the template onto which the primer hybridizes in a sequence-specific manner. These polymerases are generally commercially available, such as, for example, Taq polymerase, Klenow polymerase or reverse transcriptase.

Another advantage by comparison with the use of natural oligonucleotide primers is that the nucleic acid strand which is copied with the aid of the PNA/DNA primer and which contains the PNA part at the 5' end is stable to 5'-exonucleases. It is thus possible to degrade all natural DNA or RNA sequences in the reaction mixture by 5'-exonucleases without attack on the PNA-containing strand.

Another advantage of the PNA/DNA oligomers is that they can also be used to carry out other biochemical reactions on the DNA part which are impossible with PNAs themselves. Examples of such reactions are the 3'-tailing with 3'-terminal transferase, the digestion with restriction enzymes in the DNA double-stranded region, and ligase reactions. For example, a (PNA)-(DNA)-OH oligomer with free 3'-hydroxyl group can be linked to a second p-(DNA)-(PNA) oligomer which contains a nucleoside 5'-phosphate at the 5' end after hybridization to a complementary DNA auxiliary sequence of natural origin in the presence of a DNA ligase.

(DNA)-(PNA)-(DNA) oligomers can furthermore be incorporated into genes, which is not at present possible with PNAs.

The linkage of labeling groups onto PNA/DNA oligomers takes place by methods known per se, as described for oligonucleotides or peptides. The nature of the labeling group can vary within wide limits and depends essentially on the type of assay used. Known embodiments of gene probe assays are the hybridization protection assay, the energy transfer assay and the kissing probes assay.

PNA/DNA oligomers are additionally particularly suitable for a strand displacement assay. In many cases it is advantageous to remove the hybrid which is formed from excess gene probe with the aid of magnetic particles. The stability of the PNA/DNA gene probes according to the invention is higher than that of conventional DNA probes.

Polymerase chain reaction (PCR) and ligase chain reaction (LCR) are techniques for target amplification in which the oligomers according to the invention can likewise be used as primers. The PNA/DNA oligomers can be used particularly advantageously as gene probes on the Christmas tree principle because in this case the PNA/DNA probes can be shorter than corresponding DNA probes.

EXAMPLES

The abbreviations used for amino acids correspond to the three-letter code customary in peptide chemistry, as described in Europ. J. Biochem. 138, 9 (1984). Other abbreviations used are listed below.

Aeg N-(2-Aminoethyl)glycyl, —NH—$CH_2$—$CH_2$—NH—$CH_2$—CO—
Aeg($a^{MeOBz}$) N-(2-Aminoethyl)-N—($N^6$-(4-methoxybenzoyl)-9-adenosylacetyl)-glycyl
Aeg($c^{Bz}$) N-(2-Aminoethyl)-N-(N-4-benzoyl-1-cytosylacetyl)-glycyl
Aeg($c^{MeOBz}$) N-(2-Aminoethyl)-N—($N^4$-(4-methoxybenzoyl)-1-cytosylacetyl)-glycyl
Aeg($c^{tBuBz}$) N-(2-Aminoethyl)-N—($N^4$-(4-tert.butylbenzoyl)-1-cytosylacetyl)-glycyl
Aeg($g^{iBu}$) N-(2-Aminoethyl)-N-(N-2-isobutanoyl-9-guanosylacetyl)-glycyl
Aeg($g^{2-Ac,4-Dpc}$) N-(2-Aminoethyl)-N—($N^2$-acetyl-$O^4$-diphenylcarbamoyl-9-guanosyl)glycyl
Aeg(t) N-(2-Aminoethyl)-N-((1-thyminyl)acetyl)-glycyl
Bnpeoc 2,2-[bis(4-Nitrophenyl)]-ethoxycarbonyl)
Boc tert.-butyloxycarbonyl
BOI 2-(Benzotriazol-1-yloxy)-1,3-dimethylimidazolidinium hexafluorophosphate
BOP Benzotriazolyl-1-oxy-tris(dimethylamino)phosphonium hexafluorophosphate
BroP Bromo-tris(dimethylamino)phosphonium hexafluorophosphate
BSA N,O-bis(Trimethylsilyl)-acetamide
But tert.-butyl
Bz Benzoyl
Bzl Benzyl
Cl-Z 4-Chloro-benzyloxycarbonyl
CPG Controlled pore glass
DBU 1,8-Diazabicyclo[5.4.0]undec-7-ene
DCM Dichloromethane
Ddz 2-(3,5-Dimethoxyphenyl)-2-propyloxycarbonyl
DMF Dimethylformamide
Dmt di-(4-Methoxyphenyl)phenylmethyl
Dnpeoc 2-(2,4-Dinitrophenyl)-ethoxycarbonyl
Dpc Diphenylcarbamoyl
FAM Fluorescein residue Fm 9-Fluorenylmethyl
Fmoc 9-Fluorenylmethyloxycarbonyl
H-Aeg-OH N-(2-Aminoethyl)glycine
HAPyU O-(7-Azabenzotriazol-1-yl)-1,1,3,3-bis(tetramethylene)uronium hexafluorophosphate
HATU O-(7-Azabenzotriazol-1-yl)-1,1,3,3-tetramethyluronium hexafluorophosphate
HBTU O-(Benzotriazol-1-yl)-1,1,3,3-tetramethyluronium hexafluorophosphate
HOBt 1-Hydroxybenzotriazole
HONSu N-Hydroxysuccinimide
HOObt 3-Hydroxy-4-oxo-3,4-dihydrobenzotriazine
iBu Isobutanoyl
MeOBz 4-Methoxybenzoyl
Mmt 4-Methoxytriphenylmethyl
Moz 4-Methoxybenzyloxycarbonyl
MSNT 2-Mesitylenesulfonyl-3-nitro-1,2,4-triazole
Mtt (4-Methylphenyl)diphenylmethyl
NBA Nitrobenzyl alcohol
NMP N-Methylpyrrolidine
Obg N-(4-oxybutyl)glycyl, —O—(CH$_2$)$_4$—NH—CH$_2$—CO—
Obg(t) N-(4-oxybutyl)-N-((1-thyminyl)acetyl)-glycyl
Oeg N-(2-oxyethyl)glycyl, —O—CH$_2$—CH$_2$—NH—CH$_2$—CO—
Oeg(t) N-(2-Oxyethyl)-N-((1-thyminyl)acetyl)-glycyl
Opeg N-(5-Oxypentyl)glycyl, —O—(CH$_2$)$_5$—NH—CH$_2$—CO—
Opeg(t) N-(5-Oxypentyl)-N-((1-thyminyl)acetyl)-glycyl
Oprg N-(3-Oxypropyl)glycyl, —O—(CH$_2$)$_3$—NH—CH$_2$—CO—
Oprg(t) N-(3-Oxypropyl)-N-((1-thyminyl)acetyl)-glycyl
Pixyl 9-(9-Phenyl)xanthenyl
PyBOP Benzotriazolyl-1-oxytripyrrolidinophosphonium hexafluorophosphate
PyBroP Bromotripyrrolidinophosphonium hexafluorophosphate
TAPipU O-(7-Azabenzotriazol-1-yl)-1,1,3,3-bis (pentamethylene) uronium tetrafluoroborate
TBTU O-(Benzotriazol-1-yl)-1,1,3,3-tetramethyluronium tetrafluoroborate
tBu tert.-Butyl
tBuBz 4-tert.Butylbenzoyl
TDBTU O-(3,4-Dihydro-4-oxo-1,2,3-benzotriazin-3-yl)-1,1,3,3-tetramethyluronium tetrafluoroborate
TDO 2,5-Diphenyl-2,3-dihydro-3-oxo-4-hydroxythiophene dioxide
Teg N-(2-Thioethyl)glycyl, —S—CH$_2$—CH$_2$—NH—CH$_2$—CO—
Teg(t) N-(2-Thioethyl)-N-((1-thyminyl)acetyl)-glycyl
TFA Trifluoroacetic acid
THF Tetrahydrofuran
TNTU O-(5-Norbornene-2,3-dicarboximido)-1,1,3,3-tetramethyluronium tetrafluoroborate
TOTU O-[(Cyano(ethoxycarbonyl)methylene)amino]-1,1,3,3-tetramethyluronium tetrafluoroborate
TPTU O-(1,2-Dihydro-2-oxo-1-pyridyl)-1,1,3,3-tetramethyluronium tetrafluoroborate
Trt Trityl
TSTU O—(N-Succinimidyl)-1,1,3,3-tetramethyluronium tetrafluoroborate
Z Benzyloxycarbonyl
MS(ES$^+$) Electrospray mass spectrum (positive ion)
MS(ES$^-$) Electrospray mass spectrum (negative ion)
MS(DCI) Desorption chemical ionization mass spectrum
MS(FAB) Past atom bombardment mass spectrum Example 1

1-Hydroxy-6-((4-methoxyphenyl)-diphenylmethylamino)hexane

Mmt-hex

6-Amino-1-hexanol (1 g; 8.55 mmol) is dissolved in anhydrous pyridine (7 ml), and triethylamine (0.2 ml) is added. To this solution is added over the course of 45 minutes a solution of (4-methoxyphenyl)diphenylmethyl chloride (2.5 g; 8.12 mmol) in anhydrous pyridine (9 ml). The reaction solution is stirred further at 22° C. for 30 minutes and stopped by adding methanol (3 ml). The solution is concentrated in a rotary evaporator, and the resulting residue is coevaporated with toluene three times to remove the pyridine. The resulting residue is dissolved in ethyl acetate, and this solution is washed successively with a saturated sodium bicarbonate solution, with water and with a saturated potassium chloride solution. The organic phase is dried (Na$_2$SO$_4$), filtered and concentrated in vacuo. The crude product is purified by silica gel chromatography using heptane:ethyl acetate: triethylamine/49.5:49.5:1.

Yield: 1.64 g

MS (FAB,NBA/LiCl) 396.3 (M+Li)$^+$, 390.3 (M+H)$^+$, 273.2 (Mmt)$^+$

R$_f$ 0.44 (heptane:ethyl acetate=1:1)

Example 2

6-((4-Methoxyphenyl)diphenylmethylamino)-1-hexyl hemisuccinate

Mmt-hex-succ

1-Hydroxy-6-((4-methoxyphenyl) diphenylmethylamino) hexane (1.00 g; 2.57 mmol) is dissolved in anhydrous pyridine (10 ml). To this solution are added succinic anhydride (0.257 g; 2.57 mmol) and 4-dimethylaminopyridine (31.3 mg; 0.257 mmol). After stirring at 22° C. for 3 hours, further succinic anhydride (25.7 mg; 0.257 mmol) and 4-dimethylaminopyridine (62.6 mg; 0.56 mmol) are added, and this solution is heated at 50° C. for 6 hours. After a further 16 hours at 22° C., the mixture is concentrated, the residue is taken up in ethyl acetate, and the resulting solution is washed with ice-cold 5% strength aqueous citric acid. After the org. phase has been dried (Na$_2$SO$_4$), the solution is concentrated in a rotary evaporator. Purification of the residue by silica gel chromatography using 50% CH$_2$Cl$_2$/1% triethylamine in ethyl acetate and then using 5% methanol/1% triethylamine in dichloromethane affords the required compound as colorless oil.

MS (ES$^-$) 978.0 (2M−H)$^-$, 488.3 (M−H)$^-$

R$_f$ 0.30 (CH$_2$Cl$_2$:ethyl acetate=1:1).

Example 3

6-((4-Methoxyphenyl) diphenylmethylamino)-1-hexylsuccinylamido-Tentagel (Mmt-hex-succ-Tentagel)

The amino form of Tentagel$^R$ (Rapp polymers) (0.5 g; 0.11 mmol amino groups) is left to swell in 4-ethylmorpholine (0.1 ml) and DMF (5 ml) for 10 minutes. A solution of 6-((4- methoxyphenyl)diphenylmethylamino)-1-hexyl hemisuccinate (97.4 mg; 0.165 mmol), 4-ethylmorpholine (15.9 mg; 0.138 mmol; 17.4 ml) and TBTU (52.9 mg; 0.165 mmol) in DMF (3 ml) is then added, and the suspension is shaken at 22° C. for 16 hours. The derivatized Tentagel support is filtered off and washed successively with DMF (3×3 ml), $CH_2Cl_2$ (3×1 ml) and diethyl ether (3×1 ml) and dried. Unreacted amino groups are blocked by treatment with acetic anhydride/lutidine/1-methylimidazole in THF (1 ml) for 1 hour. The completed support is washed with $CH_2Cl_2$ (3×1 ml) and diethyl ether (3×1 ml) and dried in vacuo. Based on the monomethoxytrityl group introduced, the loading is 168 $mmolg^{-1}$.

Example 4

6-((4-Methoxyphenyl) diphenylmethylamino)-1-hexylsuccinylamidopropyl-controlled pore glass (Mmt-hex-succ-CPG)

The preparation takes place in analogy to the description in Example 3 starting from aminopropyl-CPG (supplied by Fluka) (550 Angstrom; 1.0 g) and 6-((4-methoxyphenyl)diphenylmethylamino)-1-hexyl hemisuccinate (48.7 mg; 0.082 mmol), 4-ethylmorpholine (7.6 ml) and TBTU (26.4 mg; 0.082 mmol) in DMF (3 ml). The loading of the Mmt-hex-succCPG is 91 $mmolg^{-1}$.

Example 5

N-((4-Methoxyphenyl)diphenylmethylamino)ethyl-N—($N^4$-(4-tert-butylbenzoyl)-1-cytosylacetyl)glycine (Mmt-Aeg($c^{tBuBz}$)-OH)

1.63 g (2.28 mmol) of N-((4-methoxyphenyl)diphenylmethylamino)ethyl-N—($N^4$-(4-tert-butylbenzoyl)-1-cytosylacetyl)glycine methyl ester were dissolved in a mixture of 10 ml of dioxane and 1 ml of water and, while stirring at 0° C., 4.56 ml of 1 N NaOH were added dropwise. After 2 h, the pH was adjusted to 5 by dropwise addition of 1 N $KHSO_4$, and precipitated salts were filtered off and washed with a little dioxane. The combined filtrates were evaporated in vacuo, and the residue was coevaporated twice with methanol and dichloromethane. The crude product obtained in this way was purified by chromatography on silica gel using a gradient of 2-10% methanol and 1% triethylamine in dichloromethane. The fractions containing the product were combined and concentrated in vacuo. Excess triethylamine still present was removed by coevaporation with pyridine and then toluene. 0.831 g of product was obtained as an almost white foam.

Electrospray MS (negative ion) 700.7 $(M–H)^-$.

$R_f$ 0.28 ($CH_2Cl_2$:MeOH/9:1), 0.63 ($CH_2Cl_2$:MeOH/7:3).

Example 6

N-((4-Methoxyphenyl)diphenylmethylamino)ethyl-N-((1-thyminyl)acetyl)glycine (Mmt-Aeg(t))-OH The product from the above reaction was dissolved in a mixture of 10 ml of dioxane and 2 ml of water, the solution was cooled to 0° C., and 1 N sodium hydroxide solution was added dropwise until the pH reached 11. After a reaction time of 2 h, the reaction was complete and the solution was adjusted to pH 5 by cautious addition of 2 N $KHSO_4$ solution. The solution was extracted three times with ethyl acetate, and the combined organic phases were dried over sodium sulfate and concentrated in vacuo. The crude product obtained in this way was purified by chromatography on silica gel using a gradient of 5-10% methanol and 1% triethylamine in dichloromethane. The fractions containing the product were combined and concentrated in vacuo. Excess triethylamine still present was removed by coevaporation with pyridine and then toluene. 1.065 g of product were obtained as a colorless foam.

Electrospray MS (negative ion) 1112.0 $(2M–H)^-$, 555.3 $(M–H)^-$ $R_f$ 0.28 ($CH_2Cl_2$:MeOH/8:2).

Example 7

N-((4-Methoxyphenyl)diphenylmethylamino)ethyl-N—($N^2$-isobutanoyl-9-guanosylacetyl)glycine (Mmt-Aeg($g^{iBu}$)-OH N-((4-Methoxyphenyl)diphenylmethylamino)ethyl-N—($N^2$-isobutanoyl-9-guanosylacetyl)glycine methyl ester (1.15 g; 1.72 mmol) is dissolved in dioxane (10 ml) and, at 0° C., 1 M aqueous sodium hydroxide solution (10.32 ml) is added dropwise in 5 portions over a period of 2.5 h. After a further reaction time of 2 h at room temperature, the solution is adjusted to pH 5 by dropwise addition of 2 M aqueous potassium bisulfate solution. The precipitated salts are filtered off and washed with a little dioxane. The combined filtrates are evaporated to dryness in vacuo, and the residue is coevaporated twice each with ethanol and 1/1 dichloromethane:methanol. Purification takes place by column chromatography on silica gel by elution with a gradient of 10-20% methanol in dichloromethane (with 1% triethylamine). The product is obtained as a white foam.

Yield: 1.229 g

ESMS (negative ion): 650.3 $(M–H)^-$ $R_f$ 0.25 (dichloromethane:methanol/8:2)

Example 8

N-((4-Methoxyphenyl) diphenylmethylamino)ethyl-N—($N$-$^6$-(4-methoxybenzoyl)-9-adenosylacetyl) glycine (Mmt-Aeg($a^{MeOBz}$)-OH)

N-((4-Methoxyphenyl)diphenylmethylamino)ethyl-N—($N^6$-(4-methoxybenzoyl)-9-adenosylacetyl)glycine methyl ester (1.70 g; 2.38 mmol) is dissolved in dioxane (10 ml) and, at 0° C., 1 M aqueous sodium hydroxide solution (10.32 ml) is added dropwise in 5 portions over a period of 2.5 h. After a further reaction time of 2 h at room temperature, the solution is adjusted to pH 5 by dropwise addition of 2 M aqueous potassium bisulfate solution. The precipitated salts are filtered off and washed with a little dioxane. The combined filtrates are evaporated to dryness in vacuo, and the residue is coevaporated twice each with ethanol and 1/1 dichloromethane:methanol. Purification takes place by column chromatography on silica gel by elution with a gradient of 10-20% methanol in dichloromethane (with 1% triethylamine). The product is obtained as a white foam.

Yield: 1.619 g

ESMS (negative ion): 698.3 $(M–H)^-$ $R_f$ 0.10 (dichloromethane:methanol/8:2)

Example 9

N-((4-Methoxyphenyl)diphenylmethyloxy)ethyl-N-((1-thyminyl)acetyl)glycine (Mmt-Oeg(t)-OH)

0.5 g (1.28 mmol) of N-((4-methoxyphenyl)diphenylmethyloxy)ethylglycine was suspended in 10 ml of DMF, and 0.47 ml (1.92 mmol) of BSA was added dropwise. Then, 0.7 ml (5.1 mmol) of triethylamine and 0.26 g (1.28 mmol) of chlorocarboxymethylthymine were successively added. The reaction mixture was stirred at room temperature for 4 h and then a further 65 mg (0.32 mmol) of chlorocarboxymethylthymine were added, and the mixture was stirred for 16 h. The solvent was then stripped off in vacuo, and the crude product was purified on a silica gel column using a gradient of 5-15% methanol and 1% triethylamine in dichloromethane. The fractions containing the product were combined and concentrated in vacuo. The resulting brownish oil was dissolved in a little dichloromethane, and the product was precipitated by adding diethyl ether. The product was obtained as an almost white powder.

Yield: 0.219 g
Electrospray MS (negative ion) 556.3 (M-H)$^-$.
$R_f$ 0.54 (CH$_2$Cl$_2$:MeOH/8:2).

Example 10

4-Nitrophenyl 4-(4,4'-dimethoxytrityloxy)butyrate

Dmt-but-NPE

The sodium salt of 4-hydroxybutyric acid (1.26 g; 10 mmol) is dissolved in anhydrous pyridine (30 ml), and 4,4'-dimethoxytrityl chloride (3.39 g; 3.05 mmol) is added. After 16 hours, 4-nitrophenol (1.39 g; 10 mmol) and N,N'-dicyclohexylcarbodiimide (2.06 g; 10 mmol) are added, and the mixture is stirred at 22° C. for a further 48 hours. The precipitated dicyclohexylurea is filtered off and washed with dichloromethane. The filtrate is concentrated and the resulting residue is coevaporated twice with toluene. The residue is purified on a silica gel column (10-50% ethyl acetate and 1% triethylamine in petroleum ether). The desired compound is obtained in the form of a pale yellowish-colored oil.

Yield: 2.694 g
MS (FAB, MeOH/NBA/LiCl) 534.2 (M+Li)$^+$, 527.2 M$^+$.
$R_f$ 0.34 (petroleum ether:ethyl acetate=75:25)

Example 11

H-Oprg(t)-OH 3.68 g of thyminylacetic acid are dissolved in 20 ml of dry DMF, and 6.65 g of TOTU and 2.77 ml of triethylamine are added. The mixture is stirred at room temperature for 30 min and then slowly added dropwise to a solution composed of 5.32 g of (3-hydroxypropyl)glycine, 20 ml of water, 20 ml of DMF and 5.54 ml of triethylamine. The mixture is stirred at room temperature for 1 h and then concentrated in a rotary evaporator in vacuo. The residue is taken up in water, adjusted to pH 1.5 with 1 N hydrochloric acid and extracted with ethyl acetate. The aqueous phase is adjusted to pH 5 with saturated sodium bicarbonate solution and concentrated in a rotary evaporator. The residue is mixed with 250 ml of ethanol, and the sodium chloride precipitated thereby is filtered off with suction. The filtrate is concentrated and the crude product is purified by chromatography on silica gel using dichloromethane/methanol/ethyl acetate 10:2:1 with the addition of 1% triethylamine followed by dichloromethane/methanol/ethyl acetate 10:4:1 with the addition of 1% triethylamine. The fractions containing the product are combined and concentrated in a rotary evaporator in vacuo.

Yield: 3.2 g
$R_f$ 0.15 (dichloromethane/methanol/ethyl acetate 10:2:1+1% triethylamine)
MS(ES$^+$): 300.2 (M+H)$^+$.

Example 12

Dmt-Oprg(t)-OH 3.2 g of H-Oprg(t)-OH are dissolved in 40 ml of DMF, 5.93 ml of triethylamine are added and, at 0° C., a solution of 7.25 g of Dmt-Cl in 40 ml of dichloromethane is added dropwise over the course of 20 min. The mixture is stirred at room temperature for 2 h, then the precipitated triethylamine hydrochloride is filtered off, and the filtrate is concentrated in a rotary evaporator in vacuo. The residue is taken up in dichloromethane and extracted with water, and the organic phase is dried with sodium sulfate and concentrated in a rotary evaporator in vacuo. The crude product is purified on silica gel using dichloromethane/methanol/ethyl acetate 10:2:1 with the addition of 1% triethylamine. The fractions containing the product are combined and concentrated in a rotary evaporator in vacuo.

Yield: 3.46 g
$R_f$ 0.28 (dichloromethane/methanol/ethyl acetate 10:2:1+1% triethylamine)
MS (ES$^+$) 602.4 (M+H)$^+$.

Example 13

H-Obg(t) OH 2.76 g of thyminylacetic acid are dissolved in 15 ml of dry DMF, and 4.92 g of TOTU and 2.08 ml of triethylamine are added. The mixture is stirred at room temperature for 30 min and then slowly added dropwise to a solution composed of 4.41 g of (4-hydroxybutyl)glycine, 10 ml of water, 10 ml of DMF and 4.16 ml of triethylamine. The mixture is stirred at room temperature for 3 h and then concentrated in a rotary evaporator in vacuo. The residue is taken up in water, adjusted to pH 1.5 with 1 N hydrochloric acid and extracted with ethyl acetate. The aqueous phase is adjusted to pH 5 with saturated sodium bicarbonate solution and concentrated in a rotary evaporator. The crude product is purified by chromatography on silica gel using dichloromethane/methanol/ethyl acetate 10:2:1 with the addition of 1% triethylamine. The fractions containing the product are combined and concentrated in a rotary evaporator in vacuo.

Yield: 3.7 g
$R_f$ 0.11 (dichloromethane/methanol/ethyl acetate 10:2:1+1% triethylamine)
MS (ES$^+$) 314.2 (M+H)$^+$.

Example 14

Dmt-Obg (t)-OH 3.6 g of H-Obg(t)-OH are dissolved in 40 ml of DMF, 9.5 ml of triethylamine are added and, at 0° C., a solution of 15.4 g of Dmt-Cl in 40 ml of dichloromethane is added dropwise over the course of 15 min. The mixture is stirred at room temperature for 2 h, a further 40 ml of dichloromethane are added, then the precipitated triethylamine hydrochloride is filtered off, and the filtrate is concentrated in a rotary evaporator in vacuo. The residue is taken up in dichloromethane and extracted with water, and the organic phase is dried with sodium sulfate and concentrated in a rotary evaporator in vacuo. The crude product is purified on silica gel using dichloromethane/methanol/ethyl acetate 15:1:1 with the addition of 1% triethylamine. The fractions containing the product are combined and concentrated in a rotary evaporator in vacuo.

Yield: 3.45 g $R_f$ 0.29 (dichloromethane/methanol/ethyl acetate 10:2:1+ 1% triethylamine)

MS (ES$^+$+LiCl) 622.3 (M+Li)$^+$.

Example 15

H-Opeg(t) OH 2.76 g of thyminylacetic acid are dissolved in 15 ml of dry DMF, and 4.92 g of TOTU and 2.08 ml of triethylamine are added. The mixture is stirred at room temperature for 30 min and then slowly added dropwise to a solution composed of 4.83 g of (5-hydroxypentyl)glycine, 10 ml of water, 10 ml of DMF and 4.16 ml of triethylamine. The mixture is stirred at room temperature for 3 h and then concentrated in a rotary evaporator in vacuo. The residue is taken up in water, adjusted to pH 1.5 with 1 N hydrochloric acid and extracted with ethyl acetate. The aqueous phase is adjusted to pH 5 with saturated sodium bicarbonate solution and concentrated in a rotary evaporator. The crude product is purified by chromatography on silica gel using dichloromethane/methanol/ethyl acetate 10:2:1 with the addition of 1% triethylamine. The fractions containing the product are combined and concentrated in a rotary evaporator in vacuo.

Yield: 3.34 g $R_f$ 0.19 (dichloromethane/methanol/ethyl acetate 10:2:1+ 1% triethylamine)

MS (DCl) 328.2 (M+H)$^+$.

Example 16

Dmt-Opeg(t)-OH 3.2 g of H-Opeg(t)-OH are dissolved in 40 ml of DMF, 6.77 ml of triethylamine are added and, at 0° C., a solution of 9.94 g of Dmt-Cl in 40 ml of dichloromethane is added dropwise over the course of 15 min. The mixture is stirred at room temperature for 2 h, a further 40 ml of dichloromethane are added, then the precipitated triethylamine hydrochloride is filtered off, and the filtrate is concentrated in a rotary evaporator in vacuo. The residue is taken up in dichloromethane and extracted with water, and the organic phase is dried with sodium sulfate and concentrated in a rotary evaporator in vacuo. The crude product is purified on silica gel using dichloromethane/methanol/ethyl acetate 15:1:1 with the addition of 1% triethylamine. The fractions containing the product are combined and concentrated in a rotary evaporator in vacuo.

Yield: 3.6 g $R_f$ 0.27 (dichloromethane/methanol/ethyl acetate 10:2:1+ 1% triethylamine)

MS (ES$^+$+LiCl) 636.4 (M+Li)$^+$.

Example 17

5'-ATC GTC GTA TT-(but)-agtc-hex

The DNA sequence is indicated in capital letters and the PNA sequence is indicated in small letters (example of the structural type XIIa in scheme 1). The PNAs are synthesized, for example, in an Ecosyn D-300 DNA synthesizer (from Eppendorf/Biotronik, Maintal) or an ABI 380B DNA synthesizer (from Applied Biosystems, Weiterstadt). The synthesis of the DNA part is carried out in principle by standard phosphoramidite chemistry and commercially obtainable synthesis cycles. For the synthesis of the PNA part the methods of peptide synthesis are approximated to the DNA synthesis cycles as explained hereinafter.

Scheme 1
DNA/PNA hybrid molecules

Formula XII

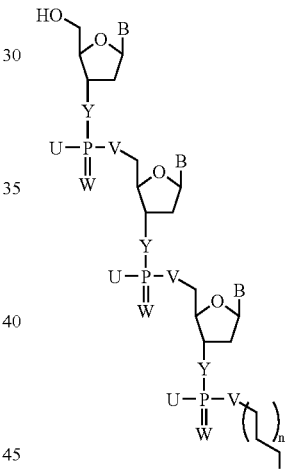

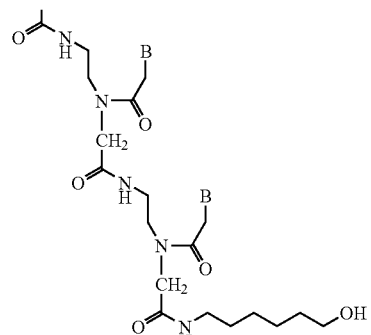

(XII a, n = 1)

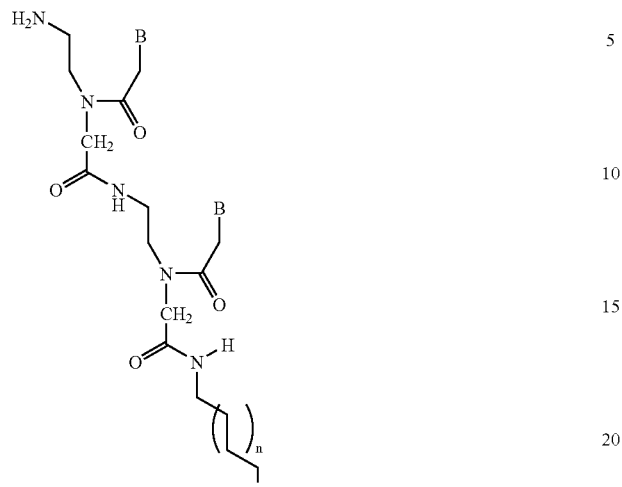
Formula XIII
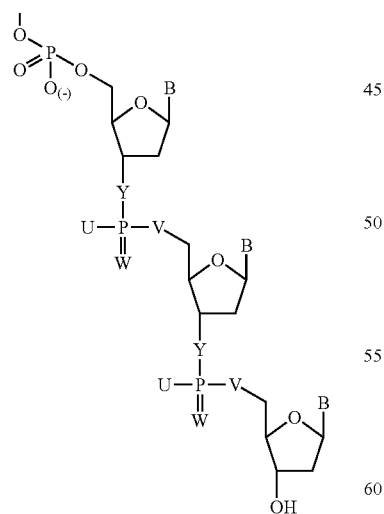
(XIII a; n = 1)

PNA/DNA hybrid Molecules
Scheme 2
Formula X
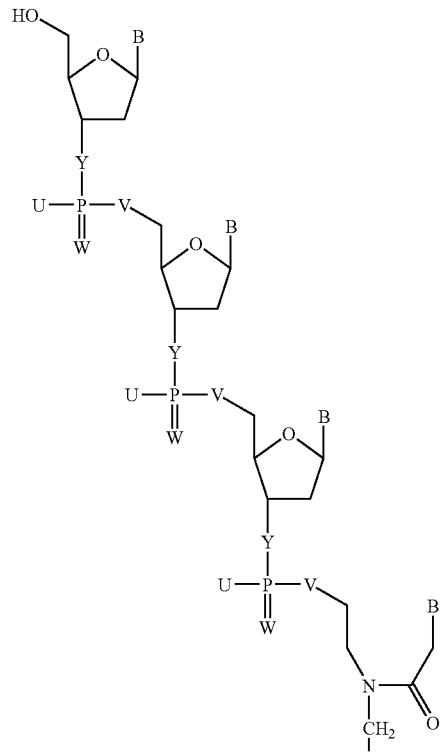
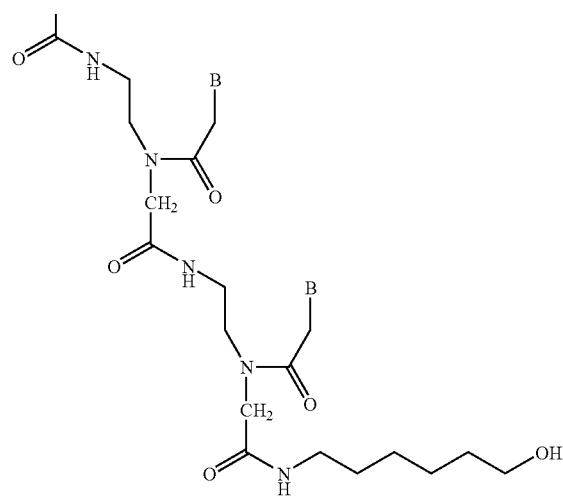
(Xa, V-O; Xb, V-NH)

-continued
Formula XI
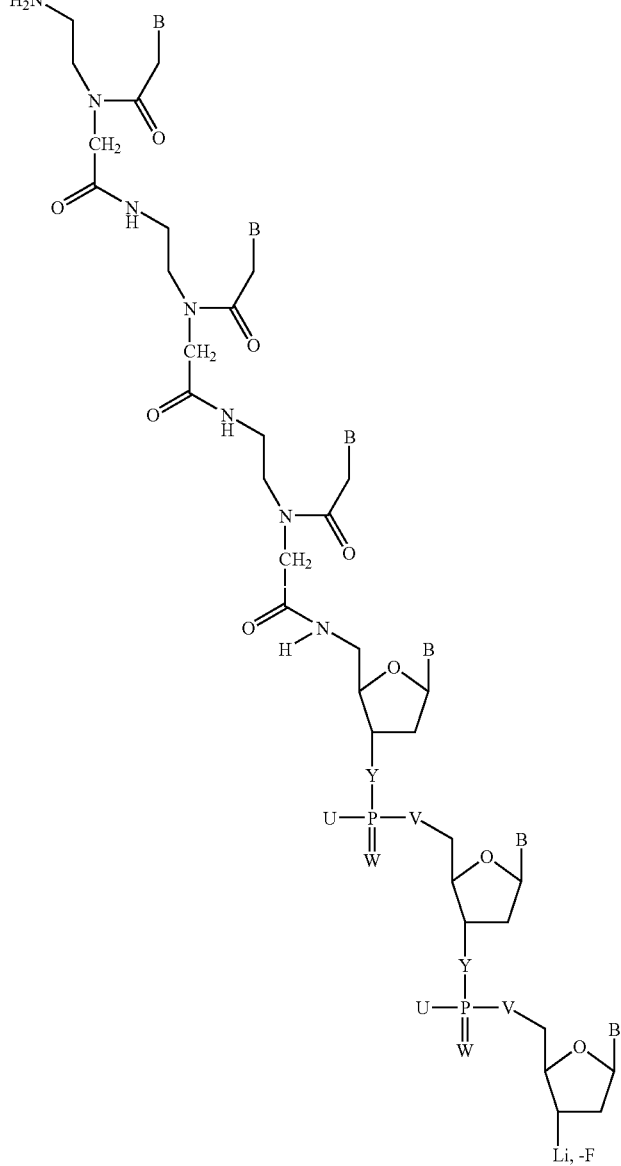
 Formula VIII
 Formula VIII
| | R⁵ | R⁶ | R² | V |
|---|---|---|---|---|
| VIII a | NC—CH₂CH₂—O— | —N(i-C₃H₇)₂ | H | O |
| VIII b | CH₃ | —N(i-C₃H₇)₂ | H | O |
| VIII c | C₆H₅ | —N(i-C₃H₇)₂ | H | O |
| VIII d | C₆H₅—C(O)—S(CH₂)₂—S | -N-pyrrolidin-1-yl | H | O |

-continued

Formula VIII

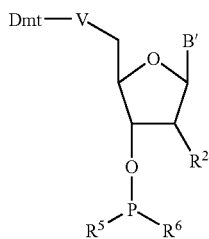

|   | R⁵ | R⁶ | R² | V |
|---|---|---|---|---|
| VIII e | NC—CH₂CH₂—O— | —N(i-C₃H₇)₂ | OCH₃ | O |
| VIII f | NC—CH₂CH₂—O— | —N(i-C₃H₇)₂ | H | NH |

Formula IX

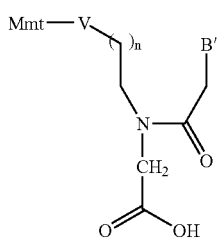

(IXa, V = NH; IXb, V = O)

with n=1-8, preferably 1-5,

Formula XIV

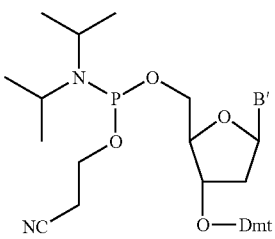

Formula XV

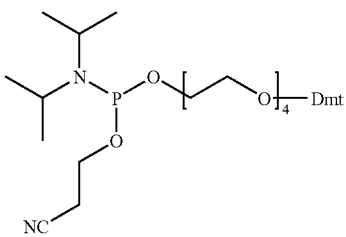

Formula XVI

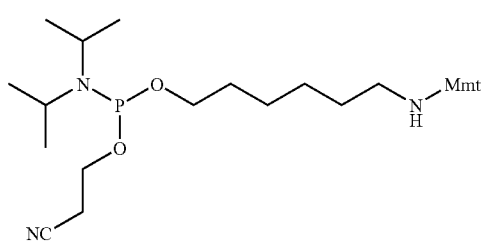

3 μmol of the CPG support loaded with Mmt-hex-succ (loading 91 μmol/g) from Example 4 are treated successively with the following reagents:

Synthesis of the PNA Part (agtc-hex):
1. dichloromethane
2. 3% trichloroacetic acid in dichloromethane
3. acetonitrile abs.
4. 3.5 M solution of 4-ethylmorpholine in acetonitrile (neutralization)
5. 0.4 X solution of (Mmt-Aeg(c$^{tBuBz}$)-OH) from Example 5 in acetonitrile:DMF=9:1/0.9 M solution of ByBOP in acetonitrile/3.5 M solution of 4-ethylmorpholine in acetonitrile (coupling time of 10 minutes).
6. step 5 is repeated four times.
7. acetonitrile Steps 1 to 7, called a PNA reaction cycle hereinafter, are repeated 3 times to assemble the PNA part, using in step 5 in each case the monomer building block, necessary according to the sequence, from Examples 5 to 8.

Conjugation of the linker (agtc-hex--->(but)-agtc-hex):
8. repeat steps 1 to 4 from above
9. 4-nitrophenyl 4-(4,4'-dimethoxytrityloxy)butyrate (105 mg) from Example 10 and hydroxybenzotriazole (27 mg) in 2 ml of NEM in DMF for 15 hours
10. wash with DMF
11. wash with acetonitrile
12. dichloromethane Synthesis of the DNA Part ((but)-agtc-hex)-->5'-ATC GTC GTA TT-(but)-agtc-hex):
13. acetonitrile abs.
14. 3% trichloroacetic acid in dichloromethane
15. acetonitrile abs.
16. 10 μmol of β-cyanoethyl 5'-O-dimethoxytritylthymidine 3'-diisopropylphosphoramidite and 50 μmol of tetrazole in 0.3 ml of acetonitrile abs.
17. acetonitrile
18. 20% acetic anhydride in THF with 40% lutidine and 10% dimethylaminopyridine
19. acetonitrile
20. iodine (1.3 g in THF/water/pyridine; 70:20:5=v:v:v)

Steps 13 to 20, called a DNA reaction cycle hereinafter, are repeated 10 times to assemble the nucleotide part, using in step 16 in each case the β-cyanoethyl 5'-O-dimethoxytrityl (nucleotide base) 3'-diisopropylphosphoramidite corresponding to the sequence.

After the synthesis is complete, the dimethoxytrityl group is eliminated as described in steps 1 to 3. The oligomer is cleaved off the support and, at the same time, the β-cyanoethyl groups are eliminated by treatment with ammonia for 1.5 hours. To eliminate the exocyclic amino protective groups, the ammoniacal solution is kept at 55° C. for 5 hours. 180 OD$_{260}$ of the resulting crude product (325 OD$_{260}$) of 5'-ATC GTC GTA TT-(but)-agtc-hex are purified by polyacrylamide gel electrophoresis. Desalting on a Biogel$^R$ column (from Biorad) results in 50 OD$_{260}$ of high-purity oligomer from this.

Example 18

5'-ATC GTC GTA TT-(Oeg(t))-agtc-hex (Example of Structural Type Xa in Scheme 2; see Example 9 for Explanation of Oeg(t))

The synthesis takes place in analogy to the description in Example 17 but in step 9 coupling the linker building block Mmt-Oeg(t)-OH from Example 9, in place of the p-nitrophenyl Dmt-butyrate, under the conditions described in step 5. 135 OD$_{260}$ of the resulting crude product (235 OD$_{260}$) of 5'-ATC GTC GTA TT-(Oeg(t)-agtc-hex are purified by polyacrylamide gel electrophoresis. Desalting on a Biogel$^R$ column (from Biorad) results in 20 OD$_{260}$ of high-purity oligomer from this.

Example 19

N-ggg g(5'NH—C)T C$_S$C$_S$A$_S$ TGG GG$_S$G$_S$ T (sequence complementary to HSV-1)

(Example of Structural Type XI in Scheme 2; $_S$ Means a Phosphorothioate Bridge; (5'NH—C) Means a 5'-aminocytidylate Residue; N Equals Amino Terminus)

The synthesis takes place starting from a CPG support on which 5'-Dmt-thymidine is bound via its 3' end. The synthesis of the DNA part is first carried out as described in Example 17 (steps 13 to 20), carrying out the oxidation in step 20 in the case of the phosphorothioate bridges ($_S$) using tetraethylthiuram disulfide (TETD; User Bulletin No. 65 of Applied Biosystems Inc.). A Dmt-protected 5'-amino-5'-deoxycytidylate 3'-phosphoramidite building block of the formula VIIIf is used as linker building block. The PNA building blocks are then condensed on in analogy to steps 1 to 7 in Example 17. After the synthesis is complete, the oligomer is cleaved off the support and, at the same time, the β-cyanoethyl groups are eliminated by treatment with ammonia for 1.5 hours. To eliminate the exocyclic amino protective groups, the ammoniacal solution is kept at 55° C. for 5 hours. Only then is the monomethoxytrityl group eliminated by treatment with 80% strength acetic acid at 22° C. for 2 hours. The product is purified by polyacrylamide gel electrophoresis and desalted on a Biogel$^R$ column (from Biorad).

Example 20

5'-G$_{Me}$G$_{Me}$G GCT CCA (Oeg(t))gg ggg t-hex (Example of Structural Type Xa in Scheme 2; $_{Me}$ Means a Methylphosphonate Bridge; see Example 9 for Explanation of Oeg(t))

The synthesis takes place in analogy to the description in Example 18 but using the appropriate methylphosphonate building blocks of the formula VIIIb in the DNA reaction cycle to incorporate the methylphosphonate bridges $_{Me}$.

Example 21

5'-C$_{S,S}$A$_{S,S}$C GT$_{S,S}$T GAG (but)Ggg cat-hex (c-myc antisense)

(Example of Structural Type XIIa in Scheme 1; $_{S,S}$ Means a Phosphorodithioate Bridge).

The synthesis takes place in analogy to the description in Example 17 but the building block VIIId is used to incorporate the dithioate bridges, and the oxidation at these sites (step 20) is carried out with TETD.

Example 22

N-cga g(5'NH-A)A CAT CA (Oeg(t))ggt cg-hex (c-fos antisense)

(5'NH-A Means 5'-amino-5'-deoxyadenylate; see Example 9 for Explanation of Oeg(t))

The synthesis takes place in analogy to the description in Example 18 with, after completion of the DNA synthesis, in analogy to Example 13 condensation on of a 5'-aminonucleotide which permits conjugation of the second PNA part. Thus, firstly six PNA synthesis cycles are carried out and then the linker building block from Example 9 is coupled on. Then seven DNA synthesis cycles are carried out, using the building block of the formula VIIIf in the last cycle. After a further four PNA synthesis cycles have been carried out, the elimination from the support and further working up are carried out as described in Example 19.

Example 23

F-cga g(5'NH-A)A CAT CAT GGT $_S$C$_S$G-O—CH$_2$CH(OH)CH$_2$—O—C$_{16}$H$_{33}$ (5'NH-A Means 5'-amino-5'-deoxyadenylate; F a fluorescein Residue on the amino terminus of the PNA and $_S$ a Phosphorothioate Bridge)

The synthesis takes place in analogy to the description in Example 19 but starting from a CPG support onto which the glycerol hexadecyl ether is bound. After 12 DNA synthesis cycles have been carried out, the linker building block VIIIf is condensed on. After four PNA synthesis cycles have been carried out and the terminal Mmt group has been eliminated, it is possible to react the free amino group quantitatively with a 30-fold excess of fluorescein isothiocyanate (FITC).

Example 24

3'-CCC TCT T-5'-(PEG)(PEG)-(Oeg(t))tg tgg g-hex (PEG Means a Tetraethylene Glycol Phosphate Residue)

The synthesis in respect of the PNA part takes place in analogy to the description in Example 17. After six PNA units have been condensed on, the (Mmt-Oeg(t)-OH) from Example 9 is coupled on. Then as linker initially the tetraethylene glycol derivative of the formula XV is condensed on twice as described in the DNA synthesis cycle before the synthesis of the DNA part with reversed orientation (from 5' to 3') is carried out. For this purpose, in place of the nucleoside 3'-phosphoramidites in each case the corresponding nucleoside 5'-phosphoramidites of the formula XIV, which are commercially available, are used in step 16 in the DNA synthesis cycles. Further deprotection and working up take place as described in Example 17.

Example 25

N-ccc tct t-(C6-link)(PEG)-3'-AAG AGG G-5'

(PEG Means a Tetraethylene Glycol Phosphate Residue; C6-Link is a 6-Aminohexanol Phosphate Residue)

The synthesis takes place in analogy to the description in Example 17 (DNA synthesis cycle) but starting from a CPG support to which 3'-O-Dmt-deoxyguanosine is bound via a 5'-O-succinate group. After six DNA units have been condensed on using the building blocks of the formula XIV, initially the tetraethylene glycol derivative of the formula XV is condensed on once as linker before coupling the phosphoramidite of the formula XVI to introduce C6-link. The PNA part is then synthesized on as in Example 17 (PNA synthesis cycle). Further deprotection and working up take place as described in Example 19.

Example 26

5'-TTT TTT TTT (but) ttt ttt-hex

The synthesis takes place in analogy to the description in Example 17. Before the product is cleaved off the support and deprotected, half the support-bound DNA/PNA hybrid is taken for fluorescence labeling (Example 27). The other half is deprotected and worked up as described in Example 17.

Example 27

(FAM is Fluorescein Residue)

5'-FAM-TTT TTT TTT (but) ttt ttt-hex

The support-bound DNA/PNA hybrid from Example 26 is fluorescence labeled by carrying out steps 13 to 20 as described in Example 17 using the fluorescein phosphoramidite from Applied Biosystems in step 16.

Example 28

5'-GGG GGG GGG (but) ttt ttt-hex

The synthesis takes place in analogy to the description in Example 17. Before the product is cleaved off the support and deprotected, half the support-bound DNA/PNA hybrid is taken for fluorescence labeling (Example 29). The other half is deprotected and worked up as described in Example 17. The title compound binds as triplex-forming oligonucleotide with high affinity to a DNA double strand which contains the homopurine motif 5'-AAA AAA GGG GGG GGG-3'.

Example 29

(FAM is Fluorescein Residue)

5'-FAM-GGG GGG GGG (but) ttt ttt-hex

The support-bound DNA/PNA hybrid from Example 28 is fluorescence labeled by carrying out steps 13 to 20 as described in Example 17 using the fluoresceine phosphoramidite from Applied Biosystems in step 16.

Example 30

Biotin-$C_{Phe}G_{Phe}$A GAA cat ca t(5'NH-G)G(Ome)U (Ome)C(Ome)-G(ome)-VitE (c-fos antisense)

(N(Ome) means a nucleotide unit N with a 2'-O-methoxy group; $_{Phe}$ means a phenylphosphonate bridge; 5'NH-G means 5'-amino-5'-deoxyguanylate).

The synthesis takes place in analogy to the description in Example 17 starting from CPG which is loaded with vitamin E (MacKellar et al. (1992) Nucleic Acids Res, 20(13), 3411-17) and coupling the building block of the formula VIIIe four times after the DNA synthesis cycle. After the 5'-aminonucleotide building block of the formula VIIIf has been coupled on, six PNA units are condensed on after the PNA synthesis cycle. After neutralization, the phosphoramidite is coupled to the amino group by a known method, and the DNA synthesis cycle is repeated appropriately to assemble the DNA part, using in the case of the phenylphosphonate bridges the building blocks of the formula VIIIc in step 16. Lastly the end group is coupled on using the biotin phosphoramidite from Glen Research. After the synthesis is complete, the oligomer is deprotected as described in Example 19, eliminating the dimethoxytrityl group at the end by treatment with 80% strength acetic acid at 22° C. for 2 hours.

Example 31

A CAT CA (Oeg(t)) ggt cg-hex (c-fos antisense)

(See Example 9 for Explanation of Oeg(t))

The synthesis takes place in analogy to the description in Example 18. In this case, firstly five PNA synthesis cycles are carried out and then the linker building block Oeg(t) from Example 9 is coupled on. Then six DNA synthesis cycles are carried out. Subsequently, the elimination from the support and the further working up are carried out as described in Example 18.

Example 32

A TAA TG (Oeg(t)) tct cg-hex (Control Oligomer for c-fos)

The synthesis takes place in analogy to the description in Example 18. In this case, firstly five PNA synthesis cycles are carried out and then the linker building block Oeg(t) from Example 9 is coupled on. Then six DNA synthesis cycles are carried out. Subsequently, the elimination from the support and the further working up are carried out as described in Example 18.

Example 33 a cat cat ggt cg-hex (c-fos Antisense)

This pure PNA oligomer was prepared as reference compound in analogy to Example 18 but with the exception that twelve PNA cycles were carried out. Deprotection of the exocyclic amino protective groups is carried out in ammoniacal solution (5 hours at 55° C.). Only then is the monomethoxytrityl group eliminated by treatment with 80% strength acetic acid at 22° C. for 2 hours.

Example 34

A (5-hexy-C)A(5-hexy-U) (5-hexy-C)A (Oeg(t)) ggt cg-hex (c-fos antisense)

(See Example 9 for Explanation of Oeg(t); 5-hexy-C Means 5-hexynylcytidine, 5-hexy-U Means 5-hexynyluridine)

The synthesis takes place in analogy to the description in Example 31 but using in place of the normal pyrimidine phosphoramidites the corresponding 5-hexynylpyrimidine nucleoside phosphoramidites in the condensation reaction.

Example 35

(PAM is Fluorescein Residue)

5'-FAM-TT (but) ttt ttt-hex

The synthesis of this PNA/DNA oligomer takes place in analogy to the description in Example 27 although only two thymidylate units are condensed on.

Example 36 taa tac gac tca cta (5'HN-T)

(5'HN-T means 5'-amino-5'-deoxythymidine)

This PNA/DNA oligomer which is composed of 15 PNA units and one nucleoside unit was synthesized as primer for the DNA polymerase reaction. This entails starting from a solid phase support (aminoalkyl-CPG) to which the 5'-monomethoxytritylamino-5'-deoxythymidine is bound via its 3'-hydroxyl group as succinate. After elimination of the monomethoxytrityl group with 3% TCA in dichloromethane, 15 PNA cycles are carried out as described in Example 17. Deprotection of the exocyclic amino protective groups is carried out in ammoniacal solution (5 hours at 55° C.). Only then is the monomethoxytrityl group eliminated by treatment with 80% strength acetic acid at 22° C. for 2 hours. A PNA/DNA oligomer with a free 3'-hydroxyl group, which is used as primer for a DNA polymerase (Klenow) is obtained.

Example 37

$p_S$-rA(2'5')rA(2'5')rA(2'5')rA-spacer-(Oeg(t)tc ctc ctg cgg-hex ($p_S$ Means a 5'-Thiophosphate; Spacer Means a Triethylene Glycol Phosphate; rA is a Riboadenylate; (2'5') Means that the Internucleotide Linkage is from 2' to 5' in the Ribose)

The synthesis of this compound takes place in analogy to the description in Example 18 by initially condensing on 14 PNA units. After the linker building block Mmt-Oeg(t)-OH from Example 9 has been introduced under the conditions described in step 5, the Mmt group is eliminated with 3% TCA, and the spacer is introduced with the aid of the commercially available Dmt-O—(CH$_2$CH$_2$O)$_3$—O—P(—OCH$_2$CH$_2$CN)N(i-C$_3$H$_7$)$_3$ spacer phosphoramidite (from Eurogentech; Brussels). The (2'5')-linked tetradenylate is synthesized on as described in Example 17 using the commercially available N$^6$-benzoyl-5'-O-Dmt-3'-O-tertbutyldimethylsilyladenosine 2'-O-cyanoethyl diisopropylaminophosphoramidite (from Milligen, Bedford, USA), extending the condensation time to 2×5 min. The stronger activator 5-ethylthiotetrazole is used in place of tetrazole in the coupling reaction. After elimination of the last Dmt group, the oligomer is phosphitylated on the 5'-OH group with bis (β-cyanoethyloxy)diisopropylaminophosphine. Oxidation with TETD and deprotection with ammonia and desilylation with fluoride result in the title compound, which stimulates RNase L.

Example 38

$p_S$-Co(2'5')Co(2'5')Co(2'5')Co-spacer-(Oeg(t))tc ctc ctg cgg-hex ($p_S$ Means a 5'-Thiophosphate; Spacer Means a Triethylene Glycol Phosphate; Co is Cordycepin (3'deoxyadenosine); (2'5') Means that the Internucleotide Linkage is from 2' to 5')

The synthesis is carried out in analogy to Example 37 but in place of the N$^6$-benzoyl-5'-O-Dmt-3'-O-tert-butyldimethyl-silyladenosine 2'-O-cyanoethyl diisopropylaminophosphoramidite, the corresponding N$^6$-benzoyl-5'-O-Dmtcordycepin 2'-O-cyanoethyl diisopropylaminophosphoramidite (from Chemogen, Konstanz) is used, and the fluoride treatment is omitted.

Example 39

5'-GG GGG GGG (Oeg(t)) ttt ttt ttt-hex

The synthesis takes place in analogy to the description in Example 18, following nine PNA couplings by condensation on of the linker building block Mmt-Oeg(t)-OH from Example 9 under the conditions described in step 5, which permits subsequent condensation of eight guanylate residues. The resulting PNA/DNA oligomer binds with high affinity in the antiparallel orientation as triplex-forming oligonucleotide to double-stranded DNA which has the sequence 5'. . . AAAAAAAAAAGGGGGGGG . . . 3'.

Example 40

Characterization of the PNA/DNA Hybrids

The characterization takes place with the aid of HPLC, polyacrylamide gel electrophoresis (PAGE) and negative ion electrospray mass spectrometry (ES–MS$^-$). The products are purified as described above and thereafter show in the PAGE (20% acrylamide, 2% bisacrylamide and 7 M urea) a single band. The RPLC takes place on RP-18 reversed phase columns from Merck (eluent A: water with 0.1% TFA, B: water/acetonitrile=1:4; linear gradient) or on a PA-100 column from Dionex (eluent A: 20 mM NaOH and 20 mM NaCl; B: 20 mM NaOH and 1.5 M NaCl; linear gradient). For the ES–MS$^-$, the PNA/DNA hybrids are converted by ammonium acetate precipitation or other metathesis into the ammonium salts. Sample introduction takes place from a solution in acetonitrile/water (1:1) containing 5 OD$_{260}$/ml oligomer. The accuracy of the method is about ±1.5 Dalton.

Example 41

Determination of Cellular Uptake and Stability after Radioactive Labeling

Radioactive Labeling:

A generally applicable labeling with $^{35}$S comprises carrying out at least one oxidation in the DNA synthesis cycle (step 20 in Example 17) for the synthesis of the DNA part using elemental sulfur-35. PNA/DNA hybrids which have a free 5'-hydroxyl group can be labeled with $^{32}$P or $^{35}$S with the aid of polynucleotide kinase by methods known per se. PNA/DNA hybrids which carry a free 3'-hydroxyl group can be labeled in a known manner with 3'-terminal transferase. As an example, the 5'-labeling of the DNA part is described here: the PNA/DNA hybrid with a free 5'-hydroxyl group (500 pmol) from Example 17, 18 or 26 is dissolved in 425 µl of water, and this solution is heated to 90° C. and rapidly cooled. Then 50 µl of 10×kinase buffer and 50 µl of $^{32}$P-gamma-ATP (6,000 Ci/mmol) or $^{35}$S-gamma-ATP are added, and the mixture is incubated at 37° C. for 1 hour. The reaction is stopped by adding 0.5 M EDTA solution. Desalting takes place with the aid of an NAP$^R$ column from Pharmacia.

Determination of Cellular Uptake:

Vero cells are incubated in DMEM, 5% FCS, in 96-well microtiter plates at 37° C. for 24 hours. After removal of the medium, the cells are washed twice with serum-free DMEM. The radioactively labeled oligomer (10$^6$ cpm) is diluted with unlabeled oligomer to a concentration of 10 µM in serum, and the cells are incubated at 37° C. therewith. 150 µl portions are removed after 1, 7 and 24 hours (called "supernatant 1"). The cells in the wells of the microtiter plates are washed 7 times with 300 μl of fresh medium, and the combined washing media (called "supernatant 2") are measured in a scintillation counter. Then 100 μl of trypsin solution are added, 30 seconds are allowed to elapse, and the supernatant is aspirated off. The cells are detached from the plate by incubating at 37° C. for 3 min. The detached cells are transferred into 1.5 ml Eppendorf tubes and centrifuged at 2,000 rpm for 6 minutes ("supernatant 3"). Supernatants 1 (5 μl), 2 and 5 (0.5 ml) are each measured separately in a scintillation counter. From this is calculated the uptake of oligomer in pmol per 100,000 cells, with supernatant 3 representing the cell-bound oligomer fraction and the total of supernatants 1 and 2 representing the non-cell-bound oligomer fraction.

Results:

| Incubation time in hours | Cellular uptake in pmol of oligomer/$10^5$ cells | |
|---|---|---|
| | PNA/DNA hybrid | DNA |
| 1 | 0.25 | 0.36 |
| 7 | 0.54 | 0.57 |
| 24 | 0.75 | 0.78 |

Investigation of the Stability of the Oligomer in Medium Containing Cells:

Supernatant 1 (10 μl) is mixed with 5 μl of 80% formamide (with Xylenecyanol and bromphenolblue), heated to 95° C. (5 minutes) and loaded onto a polyacrylamide gel (20% acrylamide, 7 M urea). After development of the gel in the electric field, the bands on the gel are assigned by autoradiography to the "stable oligomer", and the missing bands to the "degraded oligomer".

The PNA/DNA oligomer from Example 26 is 69% stable after an incubation time of 24 hours; the DNA oligomer is 3% stable.

The PNA/DNA oligomer from Example 31 has a half-life of 32 h under these conditions, whereas the corresponding DNA oligonucleotide has a half-life of about 2 h.

Example 42

Determination of Cellular Uptake by Fluorescence Labeling

COS cells are allowed to grow to confluence in Dulbecco's MEM supplemented with 10% FCS in 5 cm Petri dishes. The cells are washed twice with serum-free DMEM. A sterile needle is used to scratch an area of about 1 cm² in the middle of the Petri dish. The PNA/DNA oligomer solution (0.1 mM) to be investigated is applied to this area. Incubation is carried out at 37° C. under a $CO_2$ atmosphere. The cells are investigated by fluorescence microscopy after 2, 4 and 16 hours. For this, the cells are washed four times with serum-free DMEM, covered with a glass slide and assessed under a fluorescence microscope or by phase contrast. A fluorescence-labeled PNA (without DNA part) F-(but)-tttt ttt-hex was investigated as comparison for the PNA/DNA hybrid molecules. After the cells had been incubated with this PNA for two hours, >90% of the cells show signs of pronounced morphological changes and cell death. Most of the cells exhibit pronounced vacuolization. The plasma membrane, the cytosol and the nucleus show no uptake of PNA. After incubation with the pure PNA for a further two hours, all the cells have died. The situation is different with the DNA/PNA oligomers according to the invention. After incubation of the cells with the DNA/PNA oligomers for only two hours the cells show punctiform intracellular distribution of the PNA/DNA oligomers. The cells suffer no cell death even after prolonged incubation.

Example 43

Determination of the Melting Temperatures

The melting temperatures are determined using an HP 8452A diode array spectrophotometer, an HP 89090A Peltier element and the HP temperature control software Rev.B5.1 (from Hewlett Packard). Measurements are carried out in 0.5° C./min steps in 10 mM HEPES and 140 mM NaCl (pH 7.5) as buffer. The oligomer concentration is 0.5 to 1 $OD_{260}$ per ml.

Result for the product from Example 17 or 18 ($T_M$ with DNA)

```
5'-ATC GTC GTA T(Oeg(t))a gtc-hex    T_M = 51.5° C.

3'-TAG CAG CAT A    A T CAG-5'       antiparallel

5'-ATC GTC GTA T(Oeg(t))a gtc-hex    T_M < 20° C.

5'-TAG CAG CAT A    A T CAG-3'       parallel

5'-ATC GTC GTA TT(but)a gtc-hex      T_M = 51.0° C.

3'-TAG CAG CAT AA   T CAG-5'         antiparallel

5'-ATC GTC GTA TTA GTC-3'            T_M = 50.5° C.

3'-TAG CAG CAT AAT CAG-5'            DNA · DNA antiparallel

5'-ATC GTC GTA TT(but)a gtc-hex      T_M < 20° C.

5'-TAG CAG CAT AA   T CAG-3'         parallel
```

-continued

| Sequence | | $T_M$ with DNA | $T_M$ with RNA (T = U) |
|---|---|---|---|
| 5'-ACA TCA TGG TCG-3' DNA<br>3'-TGT AGT ACC AGC-5' | ap | 50.7° C. | 48.6° C. |
| 5-ACA TCA tgg tcg-3' (PNA/DNA)<br>3'-TGT AGT ACC AGC-5' | ap | 54.5° C. | 54.7° C. |
| 5'-ACA TCA tgg tcg-3' (PNA/DNA)<br>3'-TGT AGT ACC AGC-3' | p | 20° C. | <20° C. |
| 5'-aca tca tgg tcg-3' PNA<br>3'-TGT AGT ACC AGC-5' | ap | 58.8° C. | 66.6° C. |
| 5'-aca tca tgg tcg-3' PNA<br>5'-TGT AGT ACC AGC-3' | p | 46.3° C. | 44.8° C. |
| 5'-ACA TCA TGG TCG-3' S-DNA<br>3'-TGT AGT ACC AGC-5' | ap | 46.7° C. | 43.8° C. |

TGG TCG means a DNA part in which all internucleotide linkages are in phosphorothioate form. See page 5 for definition of p and ap.

Example 44

Tests for Antiviral Activity

The antiviral activity of the test substances on various human-pathogenic Herpesviruses is investigated in a cell culture test system. For the experiment, monkey kidney cells (Vero, $2 \times 10^5$/ml) are inoculated in serum-containing Dulbecco's MEM (5% fetal calf serum FCS) in 96-well microtiter plates and incubated at 37° C. and 5% $CO_2$ for 24 h. The serum-containing medium is then aspirated off and the cells are rinsed twice with serum-free Dulbecco's MEM (−FCS). The test substances are prediluted in $H_2O$ to a concentration of 600 μM and stored at −18° C. Further dilution steps in Dulbecco's minimal essential medium (MEM) are carried out for the test. 100 μl portions of the individual test substance dilutions are added together with 100 μl of serum-free Dulbecco's MEM (−FCS) to the rinsed cells. After incubation at 37° C. and 5% $CO_2$ for 3 h, the cells are infected with Herpes simplex virus type 1 (ATCC VR733, HSV-1 F-strain) or with Herpes simplex virus type 2 (ATCC VR734, HSV-2 G-strain) in concentrations at which the cell lawn is completely destroyed within 3 days. The infection concentration for HSV-1 is 500 plaque-forming units (PFU) per well, and for HSV-2 it is 350 PFU/well. The test mixtures then contain test substance in concentrations of 80 μM to 0.04 μM in MEM supplemented with 100 U/ml penicillin G and 100 mg/l streptomycin. All the experiments are carried out as duplicate determination with the exception of the controls which are carried out eight times per plate. The test mixtures are incubated at 37° C. and 5% $CO_2$ for 17 h. The cytotoxicity of the test substances is determined after a total incubation time of 20 h by microscopic inspection of the cell cultures. The maximum tolerated dose (MTD) is defined as the highest concentration of product which, under the stated test conditions, does not yet cause microscopically detectable cell damage. Subsequently FCS is added to a final concentration of 4%, and incubation is continued at 37° C. and 5% $CO_2$ for 55 h. The untreated infection controls then show a complete cytopathic effect (CPE). After microscopic inspection of the cell cultures they are then stained with neutral red in accordance with the vital staining method of Finter (1966). The antiviral activity of a test substance is defined as the minimum inhibitory concentration (MIC) which is needed to protect 30-60% of the cells from the cytopathogenic effect caused by the virus. The activity of the PNA/DNA chimeras is in each case better than that of the corresponding DNA oligomers or PNA oligomers.

Example 45

Determination of the in vivo Activity: Inhibition of c-Fos Protein Expression in the Rat The determination takes place as described (Sandkühler et al. (1991) in: Proceedings of the VIth World Congress on Pain, Charlton and Woolf, Editors; Elsevier, Amsterdam; pages 313-318) by superfusion of the spinal cord. After laminectomy of a barbiturate-anesthetized Sprague-Dawley rat, a two-chamber container is formed from silicone to receive the antisense oligomer. One chamber is filled with the antisense PNA/DNA derivative, while the other chamber is filled with the control oligomer (concentration of each 75 μM). The superfusate is exchanged in each case after one hour. After superfusion for 6 hours, c-fos expression is stimulated by heat treatment (52° C.) of the rear legs. Inhibition of c-fos expression can be demon-strated immunohistochemically on appropriate tissue section samples. The c-fos antisense oligonucleotide from Example 31 brings about greater inhibition of c-fos expression than does the corresponding DNA oligonucleotide and the corresponding PNA oligomer from Example 33.

Example 46

RNase H Assay

To determine the RNase H activity, 1.3 OD of the PNA/DNA oligomer to be investigated are heated with 0.5 OD of the complementary RNA sequence (target sequence) dissolved in 50 µl of autoclaved water, treated with DEPC (diethyl pyrocarbonate), at 80° C. for 5 minutes and subsequently cooled to 37° C. within 15 minutes. This results in initial denaturation of both oligomers which, after cooling, form a nucleic acid double strand in sequence-specific manner.

For the assay, this RNA.PNA/DNA duplex is incubated with 10 µl of RNase H 10× buffer, 1 µl of dithiothreitol (DTT) and 2 µl (corresponding to 10 u) of RNase H supplied by USB. The incubation mixture is made up with autoclaved, DEPC-treated water to the required total volume of 100 µl. The samples are incubated as 37° C. For the kinetic investigation, 20 µl portions of the solution were removed after 0, 2 min, 10 min and 1 h, heated at 95° C. for 5 minutes and frozen at −70° C. until analyzed. The investigation of the RNase H cleavage of RNA takes place by gel electrophoresis. It emerged that PNA/DNA hybrids which contain deoxyribonucleotide building blocks activate RNase H, with cleavage of the complementary RNA strand whereas the PNA/DNA oligomer emerges undamaged from the reaction. The cleavage reaction with the PNA/DNA oligomer takes place somewhat more slowly than with a corresponding oligodeoxyribonucleotide of equal length and sequence.

Example 47

Preparation of an HeLa Cell Extract with RNase L Activity

An HeLa cell extract was prepared in order to stimulate the activity of cellular endoribonuclease L by the 2',5'-tetraadenylate-PNA/DNA conjugates. For this purpose, 35 bottles were each charged with 20 ml of medium containing Dulbecco's MEM (mimimal essential medium) and 10% FCS (fetal calf serum). The cells can be harvested after trypsin treatment. 4 ml of cell harvest are obtained after centrifugation at 1,000 rpm. This is initially made up with 4 ml of water and, after 3 minutes, 4 ml of buffer A (5.48 g of HEPES; 15.5 g of KCl; 2.488 g of Mg acetate; 1,232 µl of 2-mercaptoethanol ad 1 l with water) are added in order to lyze the cells. The solution is then centrifuged at 30,000 rpm (about 100,000 g) in an ultracentrifuge at 0° C. for 30 minutes. The supernatant from 8 ml of cell extract is removed and stored at −20° C. for the following investigations.

Example 48

Investigation of Activiation of RNase L

For investigation of this extract for endonuclease L, initially 0.3 OD of the RNA target sequence is heated with the particular PNA/DNA oligomers at 80° C. for 5 minutes and subsequently cooled to 37° C. for the hybridization. The duplex is mixed with 20 µl of the extract, 1.2 µl of glycerol and RNase L buffer and incubated at 37° C. The total volume is then 70 µl. For the kinetic investigations, samples are removed by pipette at the times of 0, 20 and 60 minutes and heated at 95° C. for 5 minutes to denature the enzymes. The samples are lyophilized in a speedvac and analyzed by gel electrophoresis. The PNA-2',5'-tetraadenylate conjugates and tetracordycepin analogs activate cellular RNase L, whereas corresponding compounds without the tetraadenylate part do not stimulate RNase L.

Example 49

DNA Polymerase Reaction

The following 81-mer oligodeoxynucleotide is used as template for the DNA polymerase reaction:

5'-GCC CCA GGG AGA AGG CAA CTG GAC CGA AGG CGC TTG

TGG AGA AGG AGT TCA TAG CTG GGC TCC CTA TAG TGA

GTC GTA TTA-3'

The sequence of the PNA/DNA primer is:
H-taa tac gac tca cta (5NH-T)-OH 3'.

A corresponding oligodeoxynucleotide of the sequence 5'-TAA TAC GAC TCA CTA TAG-3' is used as control primer.

The primer (0.15 nmol) and the template (0.15 nmol) in 5 µl of 10×PCR buffer (500 m KCl, 100 mM tris-HCl, pH 9, 1% Triton X-100, 15 mM $MgCl_2$) are diluted with 35 µl of water and hybridized by heating to 95° C. and cooling. Then 10 µl of 2 mM dNTP mixture (nucleoside 5'-triphosphates) and 3 µl of DNA polymerase (Klenow fragment) are added, and the mixture is incubated at 22° C. and 37° C. for 0.5 hour each. The reaction solution is then analyzed on a 10% polyacrylamide gel (with 1% bis). pBR322/HaeIII digestion is loaded as marker. The reaction with the control primer shows a double-stranded DNA fragment with the expected size relative to the marker, whereas the product from the PNA/DNA primer migrates somewhat more quickly. In both cases the double strand migrates considerably faster than the template single strand in the gel electrophoresis.

The invention claimed is:

1. A gene probe assay for the determination of an oligo- or polynucleotide target (RNA or DNA), wherein the gene probe assay is homogeneous or heterogeneous and comprises hybridizing a gene probe with the oligo- or polynucleotide target, wherein the gene probe is a polyamide-oligonucleotide derivative of the formula Ia:

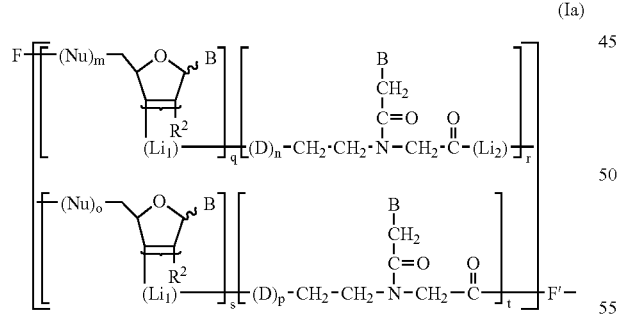

(Ia)

wherein
q=r=s=1
t =zero
$R^2$ is hydrogen, hydroxyl, $C_1$-$C_{18}$-alkoxy, halogen, azido or amino;
B is, independently of one another, a base customary in nucleotide chemistry, or a prodrug form thereof,
Nu is a radical of the formulae IIa or IIb

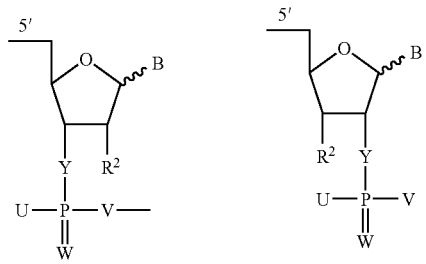

in which
$R^2$ and B are as defined above;
U is hydroxyl, mercapto, $C_1$-$C_{18}$-alkyl, $C_1$-$C_{18}$-alkoxy, $C_6$-$C_{20}$-aryl, $C_6$-$C_{14}$-aryl-$C_1$-$C_8$-alkyl, $NHR^3$ or $NR^3R^4$,
V is oxy, thio or imino;
W is oxo or thioxo;
Y is oxy, thio, methylene or imino;
D is a radical of the formula III

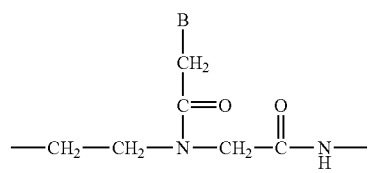

(III)

in which B is as defined above;
n is zero to 20;
p is zero to 20;

$Li_1$ and $Li_2$ are each, independently of one another, a structure of the formula V $$[(V')-(G)-(G')]_\epsilon \quad (V)$$

where, independently of one another,
$\epsilon$ is 1 to 5,
V' is oxygen, NH, a bond or a radical of the formula VI

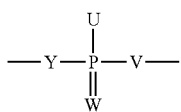

(VI)

in which U, V, W and Y are as defined above;
G can be $C_1$-$C_{12}$-alkanediyl, where alkanediyl can optionally be substituted by halogen, amino, hydroxyl, $C_1$-$C_{18}$-alkyl, $C_1$-$C_{18}$-alkoxy, $C_6$-$C_{14}$-aryl, or $C_6$-$C_{14}$-aryl-$C_1$-$C_{18}$-alkyl; $C_6$-$C_{14}$-aryl-di-$C_1$-$C_{12}$-alkanediyl, or a group of the formula $(CH_2CH_2O)_\delta CH_2CH_2$ in which $\delta$ can be 1 to 11; or a bond; and
G' is oxy, thio, imino, —C(O)—, —C(O)NH—, a bond or a radical of the formula VI in which U, V, W and Y are as defined above; and
F and F' are linked by a bond and/or
F is $R^0$-$(A)_k$-V- and
F' in formula Ia is -$(Q)^1$- $R^1$ and in formula Ib is $V^1$-$(A)_l$-$R^1$,
where
$R^0$ is hydrogen, $C_1$-$C_{18}$-alkanoyl, $C_1$-$C_{18}$-alkoxycarbonyl, $C_3$-$C_8$-cycloalkanoyl, $C_7$-$C_{15}$-aroyl, $C_3$-$C_{13}$-heteroaroyl or a group which, in the hybridization of the oligonmer onto the target nucleic acid, crosslinks with, or cleaves the target nucleic acid, or
if k is zero, $R^0$ is hydrogen or together with V is a radical of the formula VII

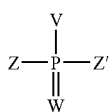

(VII)

in which Z and Z' are, independently of one another, hydroxyl, mercapto, $C_1$-$C_{22}$-alkoxy, $C_1$-$C_{18}$-alkyl, $C_6$-$C_{20}$-aryl, $C_6$-$C_{14}$-aryl-$C_1$-$C_{18}$-alkyl, $C_1$-$C_{22}$-alkylthio, $NHR^3$, $NR^3R^4$, or a group wherein intracellular uptake of the oligomer occurs or which labels a DNA probe or, in the hybridization of the oligomer onto the target nucleic acid, crosslinks with, or cleaves the target nucleic acid, and wherein
$R^3$, $R^4$, V and W are as defined above;
$R^1$ is hydrogen or $Q^o$
where $R^1$ is always only hydrogen when at the same time 1 is zero and in formula Ia t is zero and s is 1 and $Li_1$ is a structure of the formula V with V'=bond, G =bond, $\epsilon$=1 and G'=oxy, thio, imino or a radical of the formula VI with U =Z
$Q^o$ is hydroxyl, OR', $NH_2$, NHR" with
R'=$C_1$-$C_{18}$-alkyl and
R"=$C_1$-$C_{18}$-alkyl, $C_1$-$C_{18}$-aminoalkyl, $C_1$-$C_{18}$-hydroxyalkyl;
V is as defined above;
$V^1$ is a bond or V, where in F' only in formula Ib with q=zero and r=1 $V^1$ is always a bond;
k is zero to 10;
l is zero to 10;
with the proviso that
a) if in the compound of the formula Ia t is zero and s is 1, and $Li_1$ is (V')–(G)–(G') with V'=a compound of the formula VI, G =$C_2$-$C_{12}$-alkylene and G'=CO, in F'= -$(Q)_1$-$R^1$ 1 is zero to 10 and $R^1$ is $Q^o$; and
b) if in the compound of the formula Ia s=t=zero, $Li_2$ is a bond;
where each nucleotide can be in its D or L configuration, and the base can be in the $\alpha$ or $\beta$ position.

2. The gene probe assay of claim 1 wherein said B in said polyamide-oligonucleotide derivative is chosen from the group consisting of adenine, cytosine, thymine, guanine, uracil, inosine purine, 2,6 di-aminopurine, 7-deazaadenine, 7-deazaguanine, $N^4,N^4$-ethanocytosine, $N^6,N^6$-ethano-2,6-diaminopurine, pseudoisocytosine, 5-methylcytosine, 5-fluorouracil, 5-(C3-C6)-alkynyluracil, 5-(C3-C6)-alkynylcytosine and prodrug forms thereof.

3. The gene probe assay of claim 1 wherein said A and Q, independently of one another, are chosen from the group consisting of glycine, leucine, histidine, phenylalanine, cysteine, lysine, arginine, aspartic acid, glutamic acid, proline, tetrahydroisoquinoline-3-carboxylic acid, octahydroindole-2 carboxylic acid, N-(2- aminoethyl)-glycine.

4. The gene probe assay of claim 1, wherein the gene probe further comprises a detectable label.

\* \* \* \* \*